(12) United States Patent
Valkenborg et al.

(10) Patent No.: US 9,411,941 B2
(45) Date of Patent: Aug. 9, 2016

(54) METHOD AND DEVICE FOR COMPUTING MOLECULAR ISOTOPE DISTRIBUTING AND FOR ESTIMATING THE ELEMENTAL COMPOSITION OF A MOLECULE FROM AN ISOTOPIC DISTRIBUTION

(71) Applicant: Vlaamse Instelling voor Technologisch Onderzoek (VITO) NV, Mol (BE)

(72) Inventors: Dirk Valkenborg, Mol (BE); Piotr Dittwald, Mol (BE)

(73) Assignee: VLAAMSE INSTELLING VOOR TECHNOLOGISCH ONDERZOEK (VITO) NV, Mol (BE)

( * ) Notice: Subject to any disclaimer, the term of this patent is extended or adjusted under 35 U.S.C. 154(b) by 905 days.

(21) Appl. No.: 13/667,468

(22) Filed: Nov. 2, 2012

(65) Prior Publication Data
US 2013/0110412 A1    May 2, 2013

(30) Foreign Application Priority Data
Nov. 2, 2011    (EP) .................................. 11187499

(51) Int. Cl.
*H01J 49/26*     (2006.01)
*G01N 30/96*     (2006.01)
(Continued)

(52) U.S. Cl.
CPC ............. *G06F 19/70* (2013.01); *G01N 27/62* (2013.01); *G01N 30/96* (2013.01);
(Continued)

(58) Field of Classification Search
None
See application file for complete search history.

(56) References Cited

U.S. PATENT DOCUMENTS

| 7,405,409 B2 * | 7/2008 | Kearfott | G01V 5/0025 250/390.04 |
| 7,904,253 B2 | 3/2011 | Wang et al. | |
| 2008/0156997 A1 * | 7/2008 | Kearfott | G01V 5/0025 250/390.04 |

OTHER PUBLICATIONS

Book of Abstracts of the 9th Workshop on Bioinformatics and of the 4th Convention of the Polish Bioinformatics Society, *The Polish Bioinformatics Society*, Sep. 30, 2011, pp. 1-38.

(Continued)

*Primary Examiner* — Edward Cosimano
(74) *Attorney, Agent, or Firm* — Knobbe, Martens, Olson & Bear, LLP

(57) ABSTRACT

The current invention concerns a method for identifying the elemental composition of and/or quantifying the presence of mono-isotopic elements in a molecule in a sample by computing a solution of a system of linear equations $\Sigma_\alpha E_{i\alpha} n_\alpha = F_i$, whereby the set of numbers $F_i$ comprises said set of relative peak heights from the aggregated isotopic distribution and the coefficients $E_{i\alpha}$ of said linear system comprise powers and/or power sums of roots $r_{\alpha,i_\alpha}$. The present invention also provides a method for analyzing at least part of an isotopic distribution of a sample, comprising obtaining data comprising at least one probability $q_j$ with which a j'th aggregated isotopic variant of said molecule with mass number $A_j$ occurs within said aggregated isotopic distribution; and computing a probability $q_i$ with which an i'th aggregated isotopic variant occurs within said aggregated isotopic distribution, by taking a linear combination of said at least one probability $q_j$.

5 Claims, 2 Drawing Sheets

Figure 1:
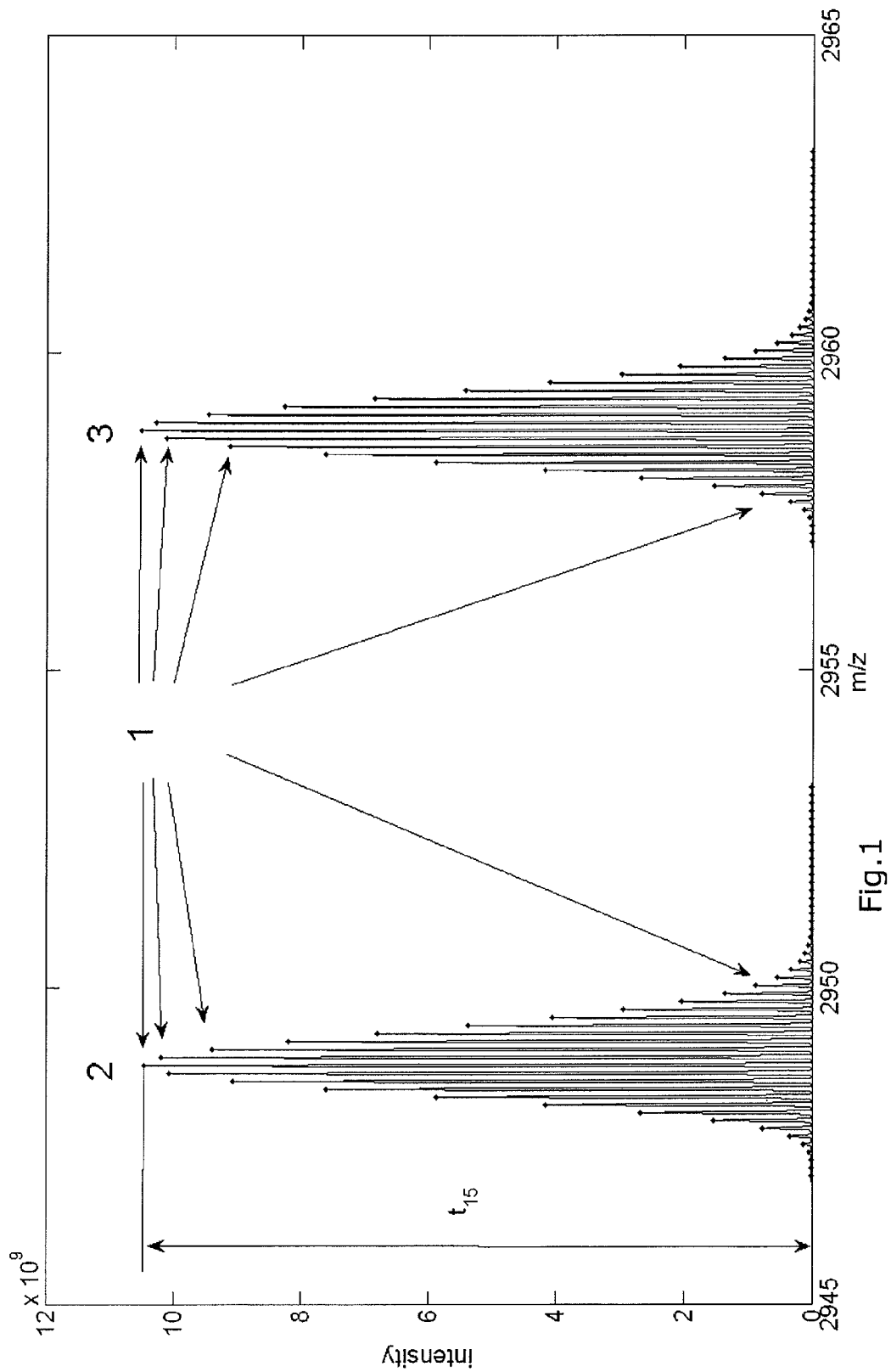

(51) Int. Cl.
*G01N 27/62* (2006.01)
*G06F 17/40* (2006.01)
*G06F 19/00* (2011.01)
*H01J 49/00* (2006.01)
*G06K 9/00* (2006.01)

(52) U.S. Cl.
CPC ............ *G06K 9/00563* (2013.01); *H01J 49/00* (2013.01); *H01J 49/004* (2013.01); *H01J 49/0036* (2013.01); *H01J 49/26* (2013.01); *G06F 17/40* (2013.01); *G06F 19/00* (2013.01)

(56) References Cited

OTHER PUBLICATIONS

Brownawell et al., "A Program for the Synthesis of Mass Spectral Isotopic Abundances," *Journal of Chemical Education*, 1982, vol. 59(8); pp. 663-665.

Claesen et al., "An Efficient Method to Calculate the Aggregated Isotopic Distribution and Exact Center—Masses", *Journal of the American Society for Mass Spectrometry*, Feb. 1 2012, published online ISSN: 1044-0305, DOI: 10.1007/s13361-011-0326-2.

Li et al., "A Hierarchical Algorithm for Calculating the Isotopic Fine Structures of Molecules," *Journal of the American Society for Mass Spectrometry*, 2008, vol. 19, pp. 1867-1874.

Li et al., "Memory-efficient calculation of the isotopic mass states of a molecule," *Rapid Communications in Mass Spectrometry*, 2010, vol. 24, pp. 2689-2696.

Olson et al., "Calculation of the Isotope Cluster for Polypeptides by Probability Grouping," *Journal of the American Society for Mass Spectrometry*, 2009, vol. 20, pp. 295-302.

Rockwood, "Relationship of Fourier Transforms to Isotope Distribution of Calculations," *Rapid Commun. Mass Spectrom.*, 1995, vol. 9, pp. 103-105.

Rockwood et al., "Ultrahigh-Speed Calculation of Isotope Distributions," *Anal. Chem.*, 1996, vol. 68, pp. 2027-2030.

Rockwood et al., "Isotopic Compositions and Accurate Masses of Single Isotopic Peaks," *J Am Soc Mass Spectrom*, 2004, vol. 15, pp. 12-21.

Rockwood et al., "Efficient Calculation of Accurate Masses of Isotopic Peaks," *J Am Soc Mass Spectrom*, 2006, vol. 17, pp. 415-419.

Rosman et al., "Isotopic Composition of the Elements 1997," *Pure and Applied Chemistry*, 1998, vol. 70(1), pp. 217-235.

Roussis et al., "Reduction of Chemical Formulas from the Isotopic Peak Distributions of High-Resolution Mass Spectra," *Analytical Chemistry*, 2003, vol. 75(6), pp. 1470-1482.

Snider, "Efficient Calculation of Exact Mass Isotopic Distributions," *Journal of the American Society for Mass Spectrometry*, 2007, vol. 18; pp. 1511-1515.

Valkenborg et al., "Using a Poisson approximation to predict the isotopic distribution of sulphur-containing peptides in a peptide-centric proteomic approach," *Rapid Communications in Mass Spectrometry*, 2007, vol. 21, pp. 3387-3391.

Valkenborg et al., "A Model-Based Method for the Prediction of the Isotopic Distribution of Peptides," *Journal of the American Society for Mass Spectrometry*, 2008, vol. 19(5), pp. 703-712.

Valkenborg et al., "The Isotopic Distribution Conundrum," *Mass Spectrometry Reviews*, May 16, 2011, vol. 31(1), pp. 96-109.

Yamamoto et al., "Calculations of Isotopic Distribution in Molecules Extensively Labeled with Heavy Isotopes," *Analytical Chemistry*, 1977, vol. 49, pp. 281-283.

Yergey, "A General Approach to Clculating Isotopic Distributions for Mass Spectrometry," *International Journal of Mass Spectrometry and Ion Physics*, 1983, vol. 52, pp. 337-349.

Yergey et al, "Isotopic Distributions in Mass Spectra of Large Molecules," Analytical Chemistry, 1983, vol. 55, pp. 353-356.

Biemann, K. "The Application of Mass Spectrometry in Organic Chemistry: Determination of the Structure of Nature Products." Angew. Chem. Internat. Edit. 1962. vol. 1, No. 2. pp. 98-111.

Macdonald, I.G. *Symmetric Functions and Hall Polynomials*. Second Edition. Oxford Mathematical Monographs. 1995.

* cited by examiner

METHOD AND DEVICE FOR COMPUTING MOLECULAR ISOTOPE DISTRIBUTING AND FOR ESTIMATING THE ELEMENTAL COMPOSITION OF A MOLECULE FROM AN ISOTOPIC DISTRIBUTION

TECHNICAL FIELD

The invention pertains to the technical field of computing the isotopic distribution of a molecule and its inverse, the identification of the elemental composition of molecules from an isotopic distribution e.g. as measured in a mass spectrometer. Furthermore, the invention pertains to the technical field of identifying the elemental composition of polypeptide molecules and, more specifically, identifying and quantifying phosphorylation events of polypeptide molecules.

BACKGROUND

Mass spectrometry (MS) is an analytical technique which was developed in the last century and which measures the mass-to-charge ratio of charged particles. It is used for determining masses of particles, for determining the elemental composition of a sample or molecule, and for elucidating the chemical structures of molecules, such as peptides and other chemical compounds. The MS principle consists of ionizing chemical compounds to generate charged molecules or molecule fragments and measuring their mass-to-charge ratios. In a typical MS procedure (i) a sample is loaded onto the MS instrument, and undergoes vaporization, (ii) the components of the sample are ionized by one of a variety of methods (e.g., by impacting them with an electron beam), which results in the formation of charged particles (ions), (iii) the ions are separated according to their mass-to-charge ratio in an analyzer by electromagnetic fields, (iv) the ions are detected, usually by a quantitative method, and (v) the ion signal is processed into mass spectra. MS instruments typically comprise three modules: (a) an ion source, which can convert gas phase sample molecules into ions (or, in the case of electrospray ionization, move ions that exist in solution into the gas phase), (b) a mass analyzer, which sorts the ions by their masses by applying electromagnetic fields, and (c) a detector, which measures the value of an indicator quantity and thus provides data for calculating the abundances of each ion present. The MS technique has both qualitative and quantitative uses. These include identifying unknown compounds, determining the isotopic composition of elements in a molecule, and determining the structure of a compound by observing its fragmentation. Other uses include quantifying the amount of a compound in a sample or studying the fundamentals of gas phase ion chemistry (the chemistry of ions and neutrals in a vacuum). MS is now in very common use in analytical laboratories that study physical, chemical, or biological properties of a great variety of compounds.

The sample which is introduced into a mass spectrometer may consist of a multitude of atoms or molecules. During the ionization step, the atoms and molecules may require a charge and may thus be easily handled by electric and magnetic fields. The charged particle is accelerated under the influence of these fields, inversely proportional to its mass-to-charge ratio m/e. A sample may consist of different molecules, with different masses. A mass spectrometer can therefore separate molecules which have masses which differ by the mass resolution width of the mass spectrometer. A typical result of a MS analysis is a mass spectrum which shows peaks at or around certain values for the mass, the peak heights at certain mass values being proportional to the amount of molecules with that mass which were present in the sample. The sample may also comprise the same molecules which are comprised of atoms which have different isotopes. The electrochemical properties of these molecules are the same, but their masses differ with an amount which is close to an integer number of atomic mass units (amu) or Daltons (Da). The different isotopes of a molecule can also be separated in a mass spectrometer since they have a different mass-to-charge ratio. Since a molecule may comprise a multitude of atoms whose isotopes occur with their elemental abundances, each molecule will have an isotopic distribution which in principle consists of a set of peak bunches whose heights depends on the atom content and atomic isotope abundances, these bunches being essentially 1 Da apart. It should be stretched that the isotopic distribution of a molecule is an identifying feature of that molecule: each molecule with a specified atomic content, i.e. with a specified molecular formula, has its characteristic isotopic distribution. Different isomers of a molecule have for all practical purposes the same isotopic distribution. When in a mass spectrum of a sample, e.g. as obtained from a MS analysis, a set of peaks is observed whose relative heights correspond to the relative heights of a molecule's isotopic distribution, one can deduce the presence of this molecule in the original sample. The absolute heights of the peaks are a quantitative measure for the amount of molecules present in the sample.

The isotopic distribution of a molecule can be computed from the molecular formula and the well-known elemental abundances and masses of the constituent atoms. The heights of the peaks in an isotopic distribution represent the probability with which the different molecular isotopes occur in nature. As an example of an isotopic distribution of a molecule, or the isotopic footprint of a molecule, one can look at carbon monoxide or CO. Carbon (C) has two naturally occurring, stable isotopes $^{12}C$ and $^{13}C$ with abundances 0.9893 and 0.0107 and with masses 12 Da and 13.0033548378 Da respectively. Oxygen (O) has three naturally occurring, stable isotopes $^{16}O$, $^{17}O$ and $^{18}O$ with abundances 0.99757, 3.8×$10^{-4}$ and 2.05×$10^{-3}$ and with masses 15.99491461956 Da, 16.99913170 Da and 17.9991610 Da respectively. The isotopic distribution comprises 6 peaks distributed in 4 bunches. The first peak is a mono-isotopic peak near mass 27.995 Da with a height of 0.986896001. This height represents the probability with which the molecular isotope of CO with one $^{12}C$ and one $^{16}O$ atom occurs in a large sample of CO molecules. The second and third peak of the CO isotopic distribution are grouped around 29 Da near masses 28.998 Da for $^{13}C^{16}O$ and 28.999 Da for $^{12}C^{17}O$ with heights 0.010673999 and 0.000375934 respectively. The fourth and fifth peak are grouped around 30 Da near masses 29.999 Da for $^{12}C^{18}O$ and 30.002 Da for $^{13}C^{17}O$ with heights 0.002028065 and 4.06600×$10^{-6}$ respectively. The sixth and last peak is again a mono-isotopic peak near mass 31.003 Da with height 2.1935×$10^{-8}$. The numbers are summarized in the following table:

| Total mass number | Mass | Abundance |
| --- | --- | --- |
| 28 | 27.995 | 0.986896001 |
| 29 | 28.998 | 0.010673999 |
| 29 | 28.999 | 0.000375934 |
| 30 | 29.999 | 0.002028065 |
| 30 | 30.002 | 0.000004066 |
| 31 | 31.003 | 0.000021935 |

From this table, it is clear that the peaks group in bunches corresponding to the total mass number, i.e. the number of nucleons present in the molecule. Obviously, the mass depends mainly on the specific isotopes of the atoms which make out the molecule. It is also clear from this example that mass spectrometers with a mass resolution which is of the order 0.002 amu or larger, will not be able to distinguish all different isotopic variants within one bunch. Instead, such mass spectrometers will show a mass spectrum with a broadened peak for each bunch whose surface below the peak will be proportional to the summed probabilities of the isotopic variants within that bunch and which will be centered around a center mass which is the weighted average of the masses of the constituting isotopic variants to a bunch, the weighting factors being proportional to the relative abundances or probabilities. This kind of bunched isotopic distribution is called the aggregated isotopic distribution. The aggregated isotopic distribution of a molecule consists of a number of peaks, each peak corresponding to a bunch of the isotopic variants of that molecule with the same total mass number, each peak being located at a center mass which is the average mass of the isotopic variants contributing to the corresponding bunch weighted by their corresponding abundances, and the height of each peaks corresponding to the sum of the abundances of the isotopic variants which contribute to the corresponding bunch.

Although access to high-resolution mass spectrometry (MS), especially in the field of biomolecular MS, is becoming readily available due to recent advances in MS technology, the accompanied information on isotopic distribution in high-resolution spectra is not used at its full potential, mainly because of lack of knowledge and/or awareness. One of the main difficulties when using MS in biomolecular MS, is that the isotopic distribution of polypeptides, which may consist of hundreds amino acids and thousands of atoms, is very hard to compute, let alone to recognize in a MS spectrum. Such a computation may require computing times which are beyond present-day capacities when a straightforward combinatorial approach is used. Furthermore, prior art techniques for identifying a molecule from an isotopic distribution may typically include a trial-and-error or fitting technique which requires a multitude of such computations.

Document U.S. Pat. No. 7,904,253B2 discloses a method for determining elemental composition of ions from mass spectral data, comprising the steps of:
  obtaining at least one accurate mass measurement from mass spectral data;
  obtaining a search list of candidate elemental compositions whose exact masses fall within a given mass tolerance range from said accurate mass;
  reporting a probability measure based on a mass error;
  calculating an isotope pattern for each candidate elemental composition from said search list;
  constructing a peak component matrix including at least one of said isotope pattern and mass spectral data;
  performing a regression against at least one of isotope pattern, mass spectral data, and the peak component matrix;
  reporting a second probability measure for at least one candidate elemental composition based on said isotope pattern regression; and
  combining the two said probability measures into an overall probability measure through the use of probability multiplications.

A limiting step in this method is the step where an isotope pattern for each candidate elemental composition from the search list is to be calculated. For very large molecules, e.g. of the order of 10000 Da, this can be a tedious and time-consuming step, even with today's computing technology. Alternatively, the isotope pattern may be obtained from a large database containing the relevant isotope patterns. However, such a database may be larger than can be stored in the e.g. the memory of a computer, especially if the molecules are large, or such a database may be incomplete. Furthermore, such a database will have to have been computed at least once. The present invention provides a method for analyzing at least part of an isotopic distribution of a sample by using i.a. a correct and efficient method for calculating an isotopic pattern of an ion e.g. for use in MS analysis or for storage in a database. More specifically, the present invention offers a method for analyzing at least part of an isotopic distribution by using a fast and efficient method for computing the aggregated isotopic distribution of a molecule. It can do this in a recursive way. The method starts by computing the center mass and probability of a starting aggregated isotopic variant of a molecule which e.g. may be expected to be present in the sample. Preferably, this starting aggregated isotopic variant is a monoisotopic variant, e.g. the lightest isotopic variant, which means that the center mass is simply the mass of the isotopic variant, and the probability is the product of the elemental abundances of the constituent atoms. From the knowledge of the probability of e.g. the lightest aggregated isotopic variant, the probability of a next aggregated isotopic variant with total mass number differing from the total mass number of the starting aggregated isotopic variant, e.g. the second lightest, can be computed. From the knowledge of the probabilities of the starting and next aggregated isotopic variant, the probability of a third aggregated isotopic variant can be computed, etc. Furthermore, the present invention also offers the possibility of computing the center mass of each aggregated isotopic variant of a molecule in a similar recursive way.

Documents Rockwood '95 (Rockwood, Alan L., Rapid Commun. Mass Spectrom. 9:103-105, 1995) and Rockwood '96 (Rockwood, Alan L., Van Orden, Steven L., Anal. Chem. 68:2027-2030, 1996) disclose a method of computing the aggregated isotopic of a molecule by casting the problem in terms of Fourier transforms. Because discrete Fourier transforms can be calculated very efficiently, this way of looking at the problem has significant practical implications. Specifically, the documents disclose an ultrahigh-speed algorithm for calculating isotope distributions from molecular formulas, elemental isotopic masses, and elemental isotopic abundances. For a given set of input data (molecular formula, elemental isotopic masses, and elemental isotopic abundances), and assuming round-off error to be negligible, the algorithm rigorously produces isotope distributions whose mean and standard deviation are "correct" in the sense that an error-free algorithm would produce a distribution having the same mean and standard deviation. The peak heights are also "correct" in the sense that the height of each nominal isotope peak from the ultrahigh-speed calculation equals the integrated peak area of the corresponding nominal isotope peak from an exact calculation. As a consequence of these properties, the algorithm generally places isotope peaks within millidaltons of their true centroids or center masses. The method uses Fourier transform methods.

Although the method introduced in Rockwood '95 and '96 is fast in computing isotopic and aggregated isotopic distributions, it may still be computationally intensive. Furthermore, this method cannot be inversed directly, i.e. when an isotopic or aggregated isotopic distribution of a molecule is presented, the Fourier Transform technique is not able to deduce the molecular formula directly: it can only deduce it through a trial-and-error or fitting technique such as the one of document U.S. Pat. No. 7,904,253B2 described here above. It is the aim of this invention to provide a method which is computationally less intensive than the Fourier transform method. Furthermore, it is the aim of this invention to provide a method which is directly invertible, i.e. which is able to deduce the molecular formula directly from a aggregated isotopic distribution without having to turn to a computationally involved and time-consuming trial-and-error method.

The prior art methods for computing the aggregated isotopic of a molecule are not fast or not accurate enough, too much memory is needed, too many details are calculated, computational problems such as numerical overflow and numerical inaccuracies can occur, etc., and this especially for large molecules such as polypeptides or oligonucleotides (DNA, RNA).

There remains a need in the art for an improved method for analyzing at least part of an isotopic distribution of a sample by computing the aggregated isotope distribution of a molecule in a more efficient, stable, computationally less intensive manner, and for an improved method for analyzing at least part of an isotopic distribution of a sample whereby the center mass of an aggregated isotopic variant is computed in an improved way. The present invention provides such methods, whereby prior art problems are overcome due to a method for computing the aggregated isotopic variant probability from previously computed or known aggregated isotopic variant probabilities. Furthermore, the center masses are computed along the same lines and do not involve a lot of extra computing time.

The present invention also provides a method for identifying the elemental composition of a molecule in a sample by inverting the presented steps for computing an aggregated isotopic distribution of a molecule, without the need of a trial-and-error or fitting technique, as is commonly used in the prior art. The present invention also provides a method for identifying and quantifying the presence of elements in a molecule, which do not alter the isotopic distribution of the molecule whilst they contribute to the mass of the molecule. Phosphor is such an element.

The present invention thus provides a transformation which calculates the aggregated isotopic distribution and exact center masses based on the elemental composition of a molecule and a method to estimate the elemental composition based on the observed aggregated isotopic distribution in a mass spectrum, by reversing said transformation. The invention claims that above tools are being used to screen for, e.g., phosphorylated peptides, or any mono-isotopic elements in a molecule. This is achieved by estimating the elemental composition from the observed aggregated isotopic distribution of a molecule. The estimated elemental composition is used to calculate the mono-isotopic mass of the observed molecule. The latter step is an addition of the mono-isotopic elemental masses. The calculated mono-isotopic mass based on the estimated elemental composition can be compared with the observed mono-isotopic mass in the mass spectrum, e.g. if the mass difference is around 31 Da, one may conclude that the observed isotope pattern is originating from a phosphorylated molecule.

Prior art techniques for identifying the elemental composition of and/or quantifying the presence of mono-isotopic elements in a molecule in a sample may involve expensive and time-consuming extra experimental steps, such as done in tandem-MS. These extra experimental steps lead to longer measuring times, extra cost, bigger equipment, etc. A trial-and-error or fitting technique is time-ineffective, especially for large molecules, for identifying the molecule from an isotope distribution. U.S. Pat. No. 7,904,253, for instance, discloses a typical trial-and-error technique for identifying the chemical formula of a molecule whose isotopic distribution has been measured in a small mass window.

The present invention aims to resolve at least some of the problems mentioned above.

There remains a need in the art for an improved method for estimating compositional information of a molecule from an isotopic distribution. The present invention provides such a method by inversing the above mentioned method. Inverting the method enables the estimation of the chemical formula of a molecule, i.e. the number of atoms of each species from an isotopic distribution. Furthermore, the present method does not need to know absolute masses, but can deal with a part of an isotopic distribution which shows only the peaks of the aggregated isotopic variants of a molecule, i.e. given the heights of a set of peaks essentially 1 Da apart, the present method is capable of computing the estimated compositional information of the molecule responsible for these peaks where atomic elements are concerned which are non-mono-isotopic in nature. For identifying mono-isotopic elements in the chemical formula of a molecule, one can use the value of the lowest, necessarily mono-isotopic mass of the molecule as derived from the estimated compositional information of the molecule and compare this with the measured value for the mass of the first peak. The difference between the observed mass in the mass spectrum and the calculated mass using the estimated compositional information gives the summed mass of all mono-isotopic elements present in the molecule which is observed.

The identification is especially hard for large molecules. Proteins and polypeptides are such large molecules, e.g. in the range of 50000 Da. A pivotal modification of polypeptides regulating many cellular activities and functions is polypeptide phosphorylation. The present invention provides a method for identifying and detecting the presence and amount of a phosphorylated polypeptide from a mass spectrometric analysis, based on the methods discussed above. Phosphorus P is a mono-isotopic element, i.e. it only has one isotope which is stable or at least stable enough to be found in naturally occurring substances.

SUMMARY OF THE INVENTION

The present invention provides a method for analysing at least part of an isotopic distribution of a sample, comprising the following steps at least once:

providing a chemical formula of a molecule;
obtaining at least part of an aggregated isotopic distribution of said molecule with said chemical formula by performing the steps of:
  obtaining data comprising at least one probability $q_j$ with which a j'th aggregated isotopic variant of said molecule with mass number $A_j$ occurs within said aggregated isotopic distribution;
  computing a probability $q_i$ with which an i'th aggregated isotopic variant of said molecule with $i>j$ and with mass number $A_i$ different from $A_j$ occurs within said aggregated isotopic distribution, characterized in that said probability $q_i$ is computed by taking a linear combination of said at least one probability $q_j$ with coefficients $C_{i,j}$, i.e. $q_i = \Sigma_{j=0}^{i-1} C_{i,j} q_j$;
comparing said aggregated isotopic distribution as obtained in the previous step, with said isotopic distribution of said sample to analyse said sample for the presence and/or quantity of said molecule. This process may also be termed feature detection and quantification by deisotoping the mass spectrum.

The present invention further provides a method for analysing at least part of an isotopic distribution of a sample as described above, whereby said one or more probabilities $q_j$ are obtained by performing the steps of:

obtaining a probability $q_0$ with which a starting aggregated isotopic variant of said molecule with mass number $A_0$ occurs in said aggregated isotopic distribution;

recursively computing probabilities $q_j$ for $j>0$ by taking linear combinations of said probability $q_0$ and previously computed probabilities $q_{j'}$ with $j'<j$ and with coefficients $C_{j,j'}$, i.e. $q_j = \Sigma_{j'=0}^{j-1} C_{j,j'} q_{j'}$.

The present invention further provides a method for analysing at least part of an isotopic distribution of a sample as described above, whereby said starting aggregated isotopic variant is a mono-isotopic variant. Both heaviest and lightest isotopic variant are composed out different elements, e.g., C,H,N,O and S. Latter poly-isotopic elements appear as a single isotope specie in the lightest and heaviest isotopic variant, i.e., they have the same nucleon count. As a consequence, the starting aggregated isotopic variant from previous paragraph does not need to be a mono-isotopic variant, i.e. $A_0$ and $q_0$ do not necessarily denote the mass number and probability of the lightest variant, but denote the mass number and probability of the starting aggregated variant, i.e. the one that needs to be calculated from first principles, taken from a database or other technique. In a preferred embodiment, said starting aggregated isotopic variant is the lightest isotopic variant. In another preferred embodiment, said starting aggregated isotopic variant is the heaviest isotopic variant.

In an embodiment of the above method for analysing at least part of an isotopic distribution of a sample, said chemical formula is described by $\Pi_\alpha (Z_\alpha)_{n_\alpha}$ with α an index running over all constituent atomic species of the molecule;

$Z_\alpha$ the α'th atomic species of the molecule; and $n_\alpha$ the number of atoms of species $Z_\alpha$ in the molecule, and said coefficients $C_{i,j}$ of said linear combination are obtained by using the steps of:

obtaining for each value of α, each root $r_{\alpha,i_\alpha}$, with $i_\alpha = 1 \ldots N_\alpha$, of an $N_\alpha$'th order elemental polynomial equation whose coefficient of the $m_\alpha$'th order term is given by an elemental abundance $P(_{Z_\alpha}^{A_\alpha + m_\alpha} Z_\alpha)$ of an isotope of the atomic species $Z_\alpha$ with $m_\alpha$ neutrons more than the lightest stable isotope of said atomic species which has atomic mass number $A_\alpha$;

computing said coefficients $C_{i,j}$ from said roots $r_{\alpha,i_\alpha}$.

For clarity, it should be mentioned here and throughout this text that α is an index for the atomic species and $A_\alpha$ here concerns the atomic mass number and not the molecular mass number of an isotopic or aggregated isotopic variant, which is indicated with Latin indices $A_i$, $A_j$, etc. Unless the context clearly dictates otherwise, Greek indices in this text are indices used in relation to atomic species, while Latin indices are numbering indices, taking on integer values, and used also for molecular or isotopic quantities, e.g.

a quantity with index α will mean that the quantity is related to the atomic species $Z_\alpha$;

$A_i$ refers to the mass number of the i'th aggregated isotope; and $i_\alpha$, as index to the roots $r_{\alpha,i_\alpha}$, takes on integer values related to atomic species $Z_\alpha$.

In a preferred embodiment, said starting aggregated isotopic variant is the lightest isotopic variant and preferably said coefficients $C_{i,j}$ are computed according to $$C_{i,j} = -\frac{1}{i}\Sigma_\alpha n_\alpha \Sigma_{i_\alpha} r_{\alpha,i_\alpha}^{-(i-j)}.$$

In a more preferred embodiment, said powers of roots $r_{\alpha,i_\alpha}^{-(i-j)}$ in the computation of said coefficients $C_{i,j}$ are computed recursively.

The present invention further provides a method for analysing at least part of an isotopic distribution of a sample as described above, whereby said chemical formula is described by $\Pi_\alpha (Z_\alpha)_{n_\alpha}$ with α an index running over all constituent atomic species of the molecule;

$Z_\alpha$ the α'th atomic species of the molecule; and $n_\alpha$ the number of atoms of species $Z_\alpha$ in the molecule, and whereby the method further comprises the steps of:

generating data comprising weighted average masses $p_i^\alpha$ of each atomic species $Z_\alpha$ within said i'th aggregated isotopic variant of said molecule with mass number $A_i$;

computing a center mass $M_i$ of said i'th aggregated isotopic variant of said molecule from said weighted average masses $p_i^\alpha$ of each atomic species $Z_\alpha$ and from said probability $q_i$.

In a preferred embodiment, said center mass $M_i$ is computed according to $M_i =$ $$\frac{1}{qi}\Sigma_\alpha n_\alpha p_i^\alpha.$$

Preferably, said at least one weight average mass $p_i^\alpha$ is computed by taking a linear combination of weighted average masses $p_j^\alpha$ of atomic species $Z_\alpha$ within aggregated isotopic variants of said molecule with mass numbers $A_j$ different from $A_i$, i.e. $p_i^\alpha = \Sigma_{j=0}^{i-1} D_{i,j}^\alpha p_j^\alpha$ with $D_{i,j}^\alpha$ the coefficients of the linear combination.

In a preferred embodiment, said weighted average mass $p_i^\alpha$ is computed recursively starting from a weighted average mass $p_0^\alpha$ of each atomic species $Z_\alpha$ within a zeroth or starting aggregated isotopic variant of said molecule with mass number $A_0$.

In a preferred embodiment, a coefficient $D_{i,j}^\alpha$ for a pre-determined value of α is obtained using the steps of:

obtaining for each value of α, each root $r_{\alpha,i_\alpha}$, with $i_\alpha = 1 \ldots N_\alpha$, of an $N_\alpha$'th-order elemental polynomial equation whose coefficient of the $m_\alpha$'th order term is given by an elemental abundance $P(_{Z_\alpha}^{A_\alpha + m_\alpha} Z_\alpha)$ of the isotope of atomic species $Z_\alpha$ with $m_\alpha$ neutrons more than the lightest stable isotope of said atomic species which has atomic mass number $A_\alpha$;

obtaining for said pre-determined value of α, each root $s_{\alpha,i_\alpha}$, with $i_\alpha = 1 \ldots N_\alpha$, of an $N_\alpha$'th-order extended polynomial equation whose coefficient of the $m_\alpha$'th-order term is given by the product of an elemental abundance $P(_{Z_\alpha}^{A_\alpha + m_\alpha} Z_\alpha)$ and the mass $M(_{Z_\alpha}^{A_\alpha + m_\alpha} Z_\alpha)$ of the isotope of atomic species $Z_\alpha$ with $m_\alpha$ neutrons more than the lightest stable isotope of said atomic species which has atomic mass number $A_\alpha$;

computing said coefficient $D_{i,j}^\alpha$ from said roots $r_{\alpha,i_\alpha}$ and $s_{\alpha,i_\alpha}$.

In a preferred embodiment, said zeroth or starting aggregated isotopic variant of said molecule is the lightest isotopic variant, and said coefficients $D_{i,j}^\alpha$ are computed according to $$D_{i,j}^a = -\frac{1}{i}\left[\Sigma_{\alpha'}\left(n_{\alpha'}\Sigma_{i_{\alpha'}} r_{\alpha',i_{\alpha'}}^{-(i-j)}\right) - r_{\alpha,i_\alpha}^{-(i-j)} + s_{\alpha,i_\alpha}^{-(i-j)}\right]$$

where $\alpha'$ is an index which runs over all atomic species constituting the molecule.

In a preferred embodiment, the powers of said roots $r_{\alpha,i_\alpha}^{-(i-j)}$ and/or $s_{\alpha,i_\alpha}^{-(i-j)}$ in the computation of said coefficients $D_{i,j}^\alpha$ are computed recursively.

The present invention further provides a device capable of analysing at least part of an isotopic distribution of a sample using any of the methods for analysing at least part of an isotopic distribution of a sample described in this document.

The present invention also provides a computer-mountable device comprising an implementation of any of the methods for analysing at least part of an isotopic distribution of a sample described in this document.

The present invention also provides a computer-mountable device comprising an implementation of any of the methods for analysing at least part of an isotopic distribution of a molecule in a sample described in this document.

The present invention also provides the use of a method for analysing at least part of an isotopic distribution of a sample as described in this document, preferably on a computer and/or a mass spectrometer and/or a peripheral instrument of a mass spectrometer.

In a further aspect, the present invention provides a method for identifying the elemental composition of and/or quantifying the presence of mono-isotopic elements in a molecule in a sample, whereby said molecule has a chemical formula $\Pi_\alpha(Z_\alpha)_{n_\alpha}$ with
- $\alpha$ an index running over a number of expected constituent atomic species of said molecule;
- $Z_\alpha$ the $\alpha$'th expected atomic species of the molecule; and
- $n_\alpha$ the number of atoms of species $Z_\alpha$ in the molecule, comprising the steps of:
- obtaining at least a part of an isotopic distribution from said sample;
- obtaining a set of $N_p$ peak heights $t_j$ with $j=1 \ldots N_p$, of at least part of an aggregated isotopic distribution from said isotopic distribution;
- computing from said set of peak heights a set of $N_p-1$ relative peak heights $\hat{t}_i$ with $i=1 \ldots N_p-1$;
- obtaining a value of $n_\alpha$ for at least one atomic species $Z_\alpha$ from said set of relative peak heights, characterized in that said value of $n_\alpha$ is obtained by computing a solution of a system of linear equations $\Sigma_\alpha E_{i\alpha}n_\alpha=F_i$, preferably this solution may be rounded to the nearest integers, whereby the set of numbers $F_i$ comprises said set of relative peak heights and the coefficients $E_{i\alpha}$ of said linear system comprise powers and/or power sums of roots $r_{\alpha,i_\alpha}$, with $i_\alpha=1 \ldots N_\alpha$, of an $N_\alpha$'th-order elemental polynomial equation whose coefficient of the $m_\alpha$'th order term is given by an elemental abundance $P(_{Z_\alpha}^{A_\alpha+m_\alpha}Z_\alpha)$ of the isotope of the atom species $Z_\alpha$ with $m_\alpha$ neutrons more than the lightest stable isotope of said atom species which has atomic mass number $A_\alpha$.

The terms "relative peak heights" and "ratios of peak heights", here and throughout this text, refer to dimensionless numbers, which can be expressed as a ratio between linear combinations of peak heights. It should be clear that the absolute value of a peak height as taken or derived from an isotopic spectrum, on itself, does not contain information on the number of a specific atomic species present within a molecule. In order to obtain information on this number, and thus on the chemical formula for the molecule, the relevant quantities should be expressed in function of ratios of linear combinations of peak heights in general, and more preferably ratios of peak heights. Thereby, a choice can be made as to which linear combination of peak heights, or which peak height is used as a reference.

In an embodiment of the method for identifying the elemental composition of and/or quantifying the presence of mono-isotopic elements in a molecule in a sample as described above, said set of peak heights $t_j$ is ordered according to the mass at which a peak height is observed. In a preferred embodiment, no peak is observed in said isotopic distribution or said aggregated isotopic distribution around a mass which is essentially 1 Da smaller than the mass at which the first of said set of peak heights $t_j$, i.e. $t_1$, is observed.

In a preferred embodiment, the masses at which the peak heights $t_j$ are observed are essentially 1 Da apart.

In a preferred embodiment, the set of $N_p-1$ relative peak heights $\hat{t}_i$ with $i=1 \ldots N_p-1$ is computed recursively from said set of $N_p$ peak heights $t_j$ with $j=1 \ldots N$, using the steps of:

$$\text{computing } \hat{t}_1 = -\frac{t_2}{t_1};$$

$$\text{computing } \hat{t}_{i+1} = -\frac{1}{t_1}\left[(i+1)t_{i+2} + \sum_{j=1}^{i}\hat{t}_{i-j+1}t_{j+1}\right]$$

for $i = 2 \ldots N_p - 1$.

Hereby, it is not necessary that $t_1$ refers to the peak height of the lightest isotope. It should be clear that any peak height can be used as reference, as well as any linear combination of peak heights. In case another peak height or linear combination of peak heights is used, the coefficients $E_{i\alpha}$ may be adapted accordingly to reflect the change in reference peak height.

In a preferred embodiment, said coefficients $E_{i\alpha}$ of said linear system are given by the sum of the $(-i)$'th power of the $N_\alpha$ roots of the $N_\alpha$'th-order elemental polynomial equation whose coefficient of the $m_\alpha$'th-order term is given by the elemental abundance $P(_{Z_\alpha}^{A_\alpha+m_\alpha}Z_\alpha)$ of the isotope of atomic species $Z_\alpha$ with $m_\alpha$ neutrons more than the lightest stable isotope of said atomic species which has atomic mass number $A_\alpha$, i.e. $E_{i\alpha}=\Sigma_{i_\alpha=1}^{N_\alpha} r_{\alpha,i_\alpha}^{-i}$, and whereby said set of numbers $F_i$ is given by said set of relative peak heights $\hat{t}_i$, i.e. $F_i=\hat{t}_i$.

In an embodiment of the method for identifying the elemental composition of and/or quantifying the presence of mono-isotopic elements in a molecule in a sample as described above, said number $N_p-1$ of relative peaks heights is at least said number of expected constituent atomic species of said molecule with two or more stable isotopes. In a more preferred embodiment, said number $N_p-1$ of relative peaks heights is at least 5, i.e. said number $N_p$, of peaks heights is at least 6, and/or said molecule comprises at most 5 atomic elements, such as C, H, N, O, S.

In an embodiment of the method for identifying the elemental composition of and/or quantifying the presence of mono-isotopic elements in a molecule in a sample as described above, said number $N_p-1$ of relative peaks heights is greater than the number of expected constituent atomic species of said molecule with two or more stable isotopes and values for $n_\alpha$ for each value of $\alpha$ are obtained by solving an over-determined system of linear equations $\Sigma_\alpha E_{i\alpha}n_\alpha=F_i$. This solution can be obtained by prior art techniques, such as a least-square solving algorithm and subsequent rounding of the resulting solutions to the nearest integers. The following non-limitative list provides still other techniques that can be used for solving the above-mentioned system of equations:

Classical Methods:
Newton
Levenberg-Marquardt
Quasi-Newton
Conjugate gradient
Nonquadratic smooth functions
Interior point methods
Active set methods
Discrete Optimization:
Mixed Integer Linear Programming
Quadratic programming
Dynamic programming
Robust Statistics:
Iteratively reweighted least-squares In an embodiment of the method for identifying the elemental composition of and/or quantifying the presence of mono-isotopic elements in a molecule in a sample as described above, said part of an isotopic distribution is provided by analysis of a mass spectrometric measurement.

In an embodiment of the method for identifying the elemental composition of and/or quantifying the presence of mono-isotopic elements in a molecule in a sample as described above, said sample comprises polypeptide molecules, lipid and/or glyco molecules.

In an embodiment of the method for identifying the elemental composition of and/or quantifying the presence of mono-isotopic elements in a molecule in a sample as described above, said expected atomic species comprise carbon, hydrogen, nitrogen, oxygen and/or sulfur.

In an embodiment of the method for identifying the elemental composition of and/or quantifying the presence of mono-isotopic elements in a molecule in a sample as described above, said molecule comprises at least one mono-isotopic constituent atom in its chemical formula, and further comprises the steps of:

obtaining from said isotopic distribution a measured mass within a precision of ±0.5 Da at which an isotope peak appears;
  computing an expected mass at which said isotope peak appears for a second molecule with a second chemical formula which is said chemical formula from which the mono-isotopic constituent atom is removed;
  comparing said measured mass with said expected mass to deduce the presence of said molecule comprising at least one mono-isotopic constituent atom in said sample.

In a preferred embodiment, said at least one mono-isotopic constituent atom is phosphorus.

In a further aspect, the present invention provides a device capable of identifying the presence, elemental composition and/or quantity of a molecule in a sample using any of the methods for identifying the elemental composition of and/or quantifying the presence of mono-isotopic elements in a molecule in a sample as described above.

In still a further aspect, the present invention provides a computer-mountable device comprising an implementation of any of the methods for identifying the elemental composition of and/or quantifying the presence of mono-isotopic elements in a molecule in a sample as described above.

In yet a further aspect, the present invention provides the use of a method for identifying the elemental composition of and/or quantifying the presence of mono-isotopic elements in a molecule in a sample as described in this document, preferably on a computer and/or a mass spectrometer and/or a peripheral instrument of a mass spectrometer.

BRIEF DESCRIPTION OF THE $D^A$ WINGS

FIG. 1 presents the aggregated isotopic distribution of beta-caseine as observed by mass spectrometry.

Figure 2:
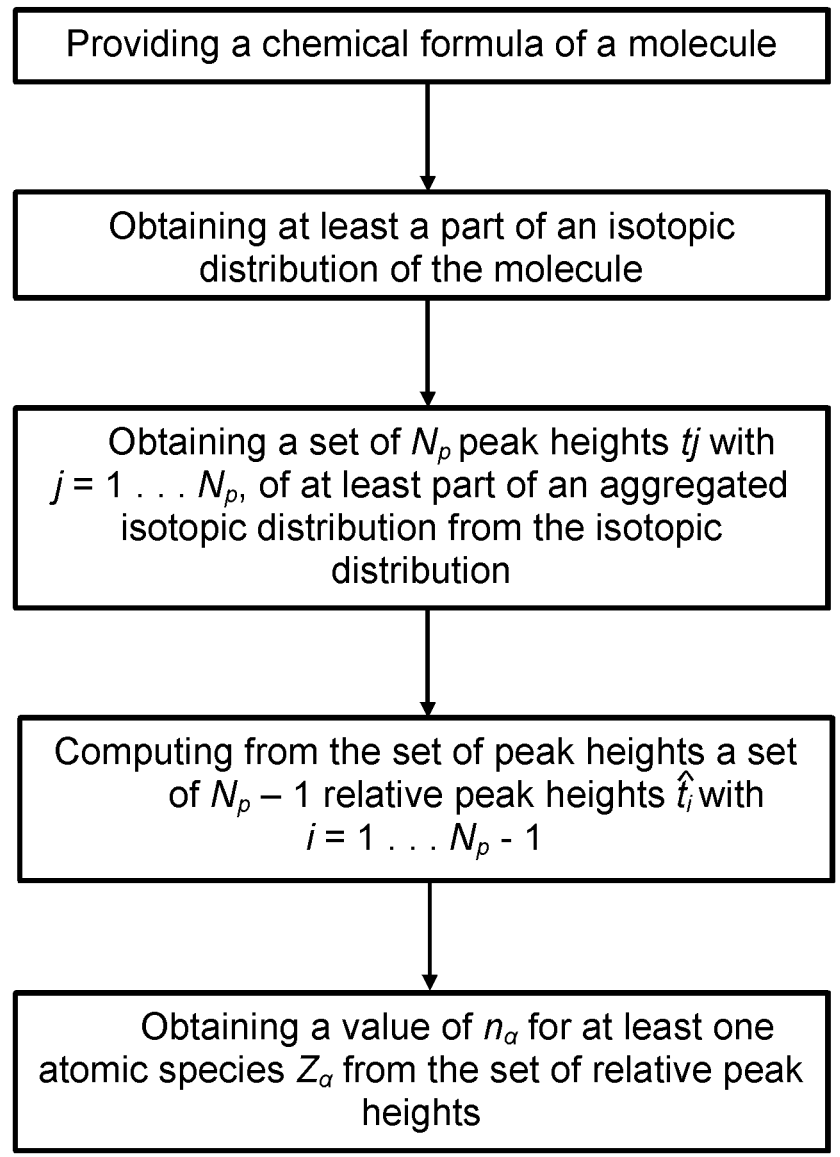

FIG. 2 is a schematic flow chart showing the steps involved in a device according to an embodiment of the present invention.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

In the following, we will give an explanation of how the method of the present invention for computing an aggregated isotopic distribution of a molecule can be derived from first principles.

The isotopic distribution is an important but often forgotten concept in the field of mass spectrometry. It is particularly useful for the interpretation of the complex patterns observed in mass spectral data. Applications can be found both in proteomics and in metabolomics. For example, a peptide molecule visualized by MS should exhibit a characteristic signal in the form of series of regularly spaced peaks. The envelope of the series of peaks displays a specific profile related to the isotopic distribution of the peptide. Prior knowledge about the isotopic distribution can be used to deconvolute the peptide patterns and to reduce the spectral information (see e.g. D. Valkenborg et al., Rapid Communications In Mass Spectrometry 21:3387-3391, 2007 and D. Valkenborg et al., Journal of the American Society for Mass Spectrometry 19(5):703-712, 2008). Another application can found in the field of metabolomics. For example, comparing the observed isotopic distribution in a mass spectrum against a set of hypothesized isotopic distributions from moieties with a similar mass as the observed molecule can increase confidence in the identification.

The reason that a molecule appears in a mass spectrum as different peaks originates from the fact that a molecule can exist as different variants with a different mass. We will denote these variants as isotope or isotopic variants. Thus, a molecule can have different isotope variants that depend on the number of different elemental isotopes incorporated into its atomic composition. The occurrence probabilities of these isotope variants are reflected in the mass spectrum, since mass spectrometry measures a population of ions of the particular molecule instead of a single ion. In this document, we present a computational and memory efficient method to calculate the probability of occurrence and exact center masses of the isotopic distribution of molecules. The calculation is based on the atomic composition of the molecule and the natural elemental abundances of the elemental isotopes in normal terrestrial matter (see e.g. in K. J. R. Rosman and P. D. P. Taylor, "Isotopic composition of the elements 1997", Pure and Applied Chemistry 70(1):217-235, 1988). Several methods have already been proposed to perform isotopic distribution calculations. These methods are proposed over a time range from the early sixties where Biemann suggested the step-wise procedure (K. Bieman, "Mass spectrometry, organic chemical application", McGraw-Hill, New York, 1962) over the late seventies where Yamamoto and McCloskey (Analytical Chemistry 49:281, 1977) and Brownawell and Fillippo (Journal of Chemical Education 59(8):663-65, 1982) argued that, for large molecules, the isotopic distribution could be easily obtained by symbolically expanding a polynomial function. Later in the eighties Yergey et al. (International Journal of Mass spectrometry and Ion Physics 52:337-349, 1983 and Analytical Chemistry 55:353-356, 1983) generalized the polynomial expansion to a multinomial expansion. An interesting overview of the different procedures to calculate isotopic distributions by Valkenborg et al. (Mass spectrometry Review, 2011, DOI 10.1002/mas.20339) is available for more insight into this matter.

In the nineties, Rockwood and co-workers propagated the use of the convolution to calculate the isotopic distribution (Rapid Communication in Mass Spectrometry 9:103-105, 1995). In their presentation of the symbolic expansion they inserted a new symbolic indicator that enabled them to relate the polynomial expansion to the convolution. We will also use this notation, but change the interpretation of the indicator such that it symbolizes the additional neutron content due to the incorporation of elemental isotopes. This implies that isotope variants with the same additional neutron content, but slightly different masses (<50 ppm), are compiled in one aggregated isotope variant. Doing so we present the information as a list of masses (m, M) of the aggregated isotope variants and their corresponding occurrence probabilities (p, q), similar in spirit as in the method of Rockwood et al. (Analytical Chemistry 68:2027-2030, 1996).

A vital element in the calculation of isotopic distributions is the assignment of the center masses to the aggregated isotope variants. To this aim the center mass can be calculated as a probability-weighted sum of the masses of the isotope combinations that contribute to this variant, as defined by Roussis and Proulx (Analytical Chemistry 75(6):14701482, 2003). However, the accuracy of this mass calculation depends on the number of isotope combinations accounted for. Rockwood et al. (Analytical Chemistry 68:2027-2030, 1996) solved this problem by a linear transformation based on the average mass and standard deviation of the isotopic distribution to acquire semi-accurate masses. Later Rockwood and colleagues focussed on accurate mass calculation of a pre-selected aggregated isotope variant (Journal of the American Society for Mass Spectrometry 15:1221, 2004 and ibidem 17:415419, 2006). Another solution to aforementioned problem was proposed by Olson and Yergey in Journal of the American Society for Mass Spectrometry 20:295302, 2009, where they propagate the idea of using equatransneutronic isotopes. However, they still observed some error in the mass assignments of the aggregated isotope variants. To overcome this inaccuracy they estimate the error and account for it in the calculation of the center masses. The method presented in this document is able to compute the exact center masses because it accumulates mass information along the recursive calculation of the isotopic distribution. In order to demonstrate its accuracy, we will compare the computed mass centers with the result obtained by the multinomial expansion of Yergey (International Journal of Mass spectrometry and Ion Physics 52:337-349, 1983) as implemented in the software package. We use the method of Yergey as a benchmark because the multinomial expansion actually reflects the physical principle behind isotope distributions.

Further, it should be mentioned that the method disclosed in this document is very suitable for isotope distributions of long biochemical molecules such as polypeptides and polynucleotides, and that most examples given in this text are constrained to isotope distribution calculations of molecules containing only carbon (C), nitrogen (N), hydrogen (H), oxygen (O) and sulfur (S). The most-abundant (and lightest) isotopes for latter elements are $_6^{12}C$, $_1^1H$, $_7^{14}N$, $_8^{16}O$ and $_{16}^{32}S$. A molecule composed out of only the previous elements is called the monoisotopic variant. In addition, we only consider stable isotopes, that is, the isotopes just mentioned, together with $_6^{13}C$, $_1^2H$, $_7^{15}N$, $_8^{17}O$, $_8^{18}O$ $_{16}^{33}S$ $_{16}^{34}S$ and $_{16}^{36}S$. Extending the presented algorithms to molecules containing other polyisotopic elements is straightforward.

Yamamoto et al. (Analytical Chemistry 49:281, 1977) and Brownawell et al. (Journal of Chemical Education 59(8):663-65, 1982) argued, that for large molecules, the isotopic forms could be easily obtained by symbolically expanding a polynomial function. In the case of proteins or peptides with a composition $C_v H_w N_x O_y S_z$, this polynomial takes the form of $$(_6^{12}C +_6^{13}C)^v \times (_1^1H +_1^2H)^w \times (_7^{14}N +_7^{15}N)^x \times (_8^{16}O +_8^{17}O +_8^{18}O)^y \times (_{16}^{32}S +_{16}^{33}S +_{16}^{34}S +_{16}^{36}S)^z. \quad (EL.1)$$

Symbolic expansion of equation (EL.1) results in many equivalent product terms, which correspond to molecules with the same mass. Collecting these equivalent product terms and substituting the probabilities of occurrence for $_6^{12}C$, $_6^{13}C$, ..., $_{16}^{36}S$ in each term separately, results in the prevalence of the isotope variants of the peptide with its corresponding mass value. The symbolic polynomial expansion was explicitly performed on computers. Although this method gives exact masses and information on the isotopic fine structure of the molecule, it has unfavorable scaling properties and a cumbersome computation process. Therefore, we claim that previous methodology is suited for the calculation of isotopic distributions for small molecules only. Contrarily, the method we propose in this document is predominantly conceived for calculating the aggregated isotope variants of large molecules. Doing so, the isotopic fine structure is ignored, but this is not an important issue since for large molecules, like e.g. intact proteins, the resolution in MS is a limitation to resolved the fine structure of aggregated isotope variants. However for large molecules the calculation of exact center masses becomes fundamental, which is taken care of by our method. When information about the isotopic fine structure is required, for example, because we use high-resolution mass spectrometry, other methods proposed by Snider (Journal of the American Society for Mass Spectrometry 18:15111515, 2007) and Li et al. (Journal of the American Society for Mass Spectrometry 19:18671874, 2008 and Rapid Communications in Mass Spectrometry 24:26892696, 2010) are available. If the molecule is not too large then the previous method or the multinomial expansion of Yergey may be used.

In order to make abstraction of the isotope masses, we introduce an indicator variable (polynomial in variable 1) to equation (EL.1), which projects the calculation of the isotopic distribution in terms of the additional neutron content, i.e., aggregated isotopic distribution. This can be written as follows:

$$(P(_6{}^{12}C)I^0 + P(_6{}^{13}C)I^1)^v \times (P(_1{}^1H)I^0 + P(_1{}^2H)I^1)^w \times (P(_7{}^{14}N)I^0 + P(_7{}^{15}N)I^1)^x \times (P(_8{}^{16}O)I^0 + P(_8{}^{17}O)I^1 + P(_8{}^{18}O)I^2)^y \times (P(_{16}{}^{32}S)I^0 + P(_{16}{}^{33}S)I^1 + P(_{16}{}^{34}S)I^2 + P_{16}{}^{36}S)I^4)^z, \quad (EL.2)$$

where the terms $P(_6{}^{12}C)$, $P(_1{}^1H)$, $P(_7{}^{14}N)$, $P(_8{}^{16}O)$ and $P(_{16}{}^{32}S)$ represent the occurrence probabilities of element's natural abundances in normal terrestrial matter, as displayed in Table (ELT.1). Note that the power of the symbolic indicator/represents the additional neutron content (or discrete mass shift) with respect to the monoisotopic variant. The indicator I is our new book keeping device instead of the symbols in the expansion of equation (EL.1) and tracks the different aggregated isotope variants. It should be stressed that equation (EL.2) makes abstraction of the mass information as the aggregated isotope variants are presented by their additional neutron count.

TABLE (ELT. 1)

Standard atomic weights (IUPAC 1997, K. J. R. Rosman and P. D. P. Taylor, "Isotopic composition of the elements 1997", Pure and Applied Chemistry 70(1): 217-235, 1988) for the isotopes of elements as they exist naturally in normal terrestrial material.

| Isotope | Atomic mass (ma/u) | Natural abundance (atom %) |
|---|---|---|
| Carbon | | |
| $_6{}^{12}C$ | 12.0000000000 | 98.93 |
| $_6{}^{13}C$ | 13.0033548378 | 1.07 |
| Hydrogen | | |
| $_1{}^1H$ | 1.0078250321 | 99.9885 |
| $_1{}^2H$ | 2.0141017780 | 0.0115 |
| Nitrogen | | |
| $_7{}^{14}N$ | 14.0030740052 | 99.632 |
| $_7{}^{15}N$ | 15.0001088984 | 0.368 |
| Oxygen | | |
| $_8{}^{16}O$ | 15.9949146 | 99.757 |
| $_8{}^{17}O$ | 16.9991312 | 0.038 |
| $_8{}^{18}O$ | 17.9991603 | 0.205 |
| Sulfur | | |
| $_{16}{}^{32}S$ | 31.97207070 | 94.93 |
| $_{16}{}^{33}S$ | 32.97145843 | 0.76 |
| $_{16}{}^{34}S$ | 33.96786665 | 4.29 |
| $_{16}{}^{36}S$ | 35.96708062 | 0.02 |

The polynomial in equation (EL.2) can be represented in several forms. For example, the polynomial at the left-hand side of equation (EL.3) in its simple form, can be written as a sum of powers of I in its expanded form; The expanded form can be seen in the right-hand side of equation (EL.3).

$$(aI^0 \pm bI^1 + cI^2)^3 = q_0 I^0 + q_1 I^1 + q_2 I^2 + q_3 I^3 + q_4 I^4 + q_5 I^5 + q_6 I^6 \quad (EL.3)$$

It is obvious that both terms are equivalent. Now the trick will be to calculate the coefficients $q_0, \ldots, q_5$, which are in function of a, b and c. However, even for this seemingly simple example, the result can already be quite complex, as shown in equation (EL.4).

$$q_0 = a^3\ q_1 = 3a^2 b\ q_2 = 3a^2 c + 3ab^2\ q_3 = b^3 + 6abc\ q_4 = 3b^2 c + 3ac^2\ q_5 = 3bc^2\ q_6 = c^3 \quad (EL.4)$$

Note that the solution in equation (EL.4) is identical to the aggregated isotopic distribution of an ozon molecule ($O_3$). Of course the coefficients a, b and c should be replaced by the occurrence probabilities of $_8{}^{16}O$, $_8{}^{17}O$ and $_8{}^{18}O$ respectively.

More generally, the polynomial in equation (EL.2) can be expressed as $$Q(I;v,w,x,y,z) = \Sigma_{i=0}^n q_i I^i \quad (EL.5)$$

where n=v+w+x+2y+4z denotes the largest power, which is a function of the atomic composition of the molecule. Hence, the problem of calculating the isotopic distribution may be reformulated as the problem of finding coefficients $q_i$ for i=0 ... n of the expanded polynomial. In principle, the coefficients $q_i$ represent the occurrence probability of the i-th aggregated isotope variant and can be obtained by $$q_i = \Sigma_j p_{ij} \quad (EL.6)$$

where $p_{ij}$ denote the probabilities of all j isotope variants with i additional neutrons. Unfortunately, in order to calculate the sum in equation (EL.6), we need to know all possible isotope variants contributing to the i-th aggregated variant. This can be achieved via the solution of a Diophantine equation, which is a cumbersome and computational intensive process. Later on, we will outline how these coefficients can be calculated in a mathematical elegant manner by using the properties of elementary symmetric polynomials and power sums of the roots of the polynomial in equation (EL.2). The method avoids the solution of the Diophantine equation.

Based on an adaptation of the Newton-Girard theorem and Viete's formulas (see e.g. I. G. Macdonald, "Symmetric functions and Hall polynomials", Clarendon Press, Oxford University Press, Oxford:New York, 1979), we can express the coefficients $q_i$ in term of the power sums of the roots $\rho_{-1}, \rho_{-2}, \ldots$ of the polynomial in equation (EL.2) and the coefficient $q_0, \ldots, q_{i-1}$:

$$q_i = \sum_{j=0}^{i-1} C_{i,j} q_j \quad (1)$$

with $$C_{i,j} = -\frac{1}{i} \rho_{-(i-j)} \quad (2)$$

and therefore $$q_i = -\frac{1}{i} \sum_{j=0}^{i-1} \rho_{-(i-j)} q_j \quad (EL.7)$$

the terms $q_i$ are the coefficients of the expanded polynomial and correspond here to the probability of occurrence of the aggregated isotope variant with i additional neutrons. This is a recursive equation, which starts with the coefficient $q_0$. The coefficient $q_0$ can be easily calculated as it corresponds to the probability of the monoisotopic variant. As pointed out by Beynon, the probability that no heavy isotopes would occur in a peptide of composition $C_vH_wN_xO_yS_z$ was $$q_0 = P(_6^{12}C) \times P(_1^1H) \times P(_7^{14}N) \times P(_8^{16}O) \times P(_{16}^{32}S) \qquad \text{(EL.8)}$$

In the next step we need to calculate the power sum of the roots $\rho_{-1}, \rho_{-2}, \ldots$ of the polynomial (EL.2). These terms can be computed in advance using the logarithmic transformation for improved numerical stability and stored on the computer for consecutive calculation steps.

However, one may rewrite the recursive relation of equations (1), (2) and (EL.7) in matrix form as:

$$\begin{bmatrix} q_1 \\ q_2 \\ \vdots \\ q_n \end{bmatrix} = \begin{bmatrix} C_{1,0} & 0 & \ldots & 0 \\ C_{2,0} & C_{2,1} & \ldots & 0 \\ \vdots & \vdots & \ddots & \vdots \\ C_{n,0} & C_{n,1} & \ldots & C_{n,n-1} \end{bmatrix} \begin{bmatrix} q_0 \\ q_1 \\ \vdots \\ q_{n-1} \end{bmatrix} \qquad \text{(M3)}$$

where the coefficient matrix is a lower triangular matrix. It should be clear to the skilled person that one can compute any $q_j$ with $i > 0$ as a proportion of the value for $q_0$ using e.g. a forward substitution algorithm, without the necessity of having to compute all intermediate $q_j$'s with $0 < j < i$. This also means that it is not necessary to start from the value of $q_0$ to compute all $q_i$'s, one may equally start from any $q_i$ with $i > 0$. This may be illustrated more easily by rewriting the recursive relation of equations (1), (2), (EL.7) and (M3) as $$Q \equiv \begin{bmatrix} q_0 \\ q_1 \\ q_2 \\ \vdots \\ q_n \end{bmatrix} = \begin{bmatrix} 1 & 0 & 0 & \ldots & 0 \\ C_{1,0} & 0 & 0 & \ldots & 0 \\ C_{2,0} & C_{2,1} & 0 & \ldots & 0 \\ \vdots & \vdots & \ddots & \ddots & \vdots \\ C_{n,0} & C_{n,1} & \ldots & C_{n,n-1} & 0 \end{bmatrix} \begin{bmatrix} q_0 \\ q_1 \\ q_2 \\ \vdots \\ q_n \end{bmatrix} \qquad \text{(M4)}$$

which can be rewritten as $$eQ = \begin{bmatrix} 0 & 0 & 0 & \ldots & 0 \\ C_{1,0} & -1 & 0 & \ldots & 0 \\ C_{2,0} & C_{2,1} & -1 & \ldots & 0 \\ \vdots & \vdots & \ddots & \ddots & \vdots \\ C_{n,0} & C_{n,1} & \ldots & C_{n,n-1} & -1 \end{bmatrix} \begin{bmatrix} q_0 \\ q_1 \\ q_2 \\ \vdots \\ q_n \end{bmatrix} = 0 \qquad \text{(M5)}$$

The solution of this set of linear equations is given by the null space of the matrix $e$. If the numbers $q_0, q_1, \ldots, q_n$, are taken as the (n+1) coordinate numbers in a (n+1)-dimensional space, the solution for equation (M5) is given by all vectors along one single direction in this (n+1)-dimensional solution space. This can be observed from the form of the matrix $e$ which clearly has n linearly independent rows and 1 dependent row: the first one with all zeroes. The null space of the matrix $e$ is thus one-dimensional. The direction in the (n+1) dimensional space which defines the null space is determined by a (n+1)-dimensional vector whose components are proportional to the probabilities $q_i$, $i = 0 \ldots n$ Therefore, all probabilities $q_j$, $i = 0 \ldots n$ can be obtained once a solution to eq. (M5) is found and only one probability, e.g. $q_0$ but any one probability will do, is known. A solution of eq. (M5) can be found using a large number of techniques known in the art: Gaussian elimination can be used, but may lead to numerical accuracy problems due to rounding errors for large matrices; singular value decomposition (SVD) is a state-of-the-art technique which keeps numerical inaccuracies under control and can also be used to find the kernel or null space of the matrix $e$; the well-known QR-decomposition may also be used, etc.

The above discussion illustrates that it is not necessary to start with the probability of the lightest isotopic variant $q_0$, when computing the aggregated isotopic distribution of a molecule. By performing well-known linear operations on the matrix $e$, such as taking linear combinations of rows or columns, on may put the matrix $e$ in such a form as to allow one to start with any $q_i$, e.g. $q_1$ in which case the equation (M5) may be left-multiplied by the invertible matrix $$\begin{bmatrix} 1 & -\frac{1}{C_{1,0}} & 0 & \ldots & 0 \\ C_{1,0} & 0 & 0 & \ldots & 0 \\ 0 & 0 & 1 & \ldots & 0 \\ \vdots & \vdots & & \ddots & \vdots \\ 0 & 0 & \ldots & 0 & 1 \end{bmatrix} \qquad \text{(M6)}$$

which leads to a set of equations $e'Q = 0$, with $$e' = \begin{bmatrix} -1 & \frac{1}{C_{1,0}} & 0 & \ldots & 0 \\ 0 & 0 & 0 & \ldots & 0 \\ C_{2,0} & C_{2,1} & -1 & \ldots & 0 \\ \vdots & \vdots & \ddots & \ddots & \vdots \\ C_{n,0} & C_{n,1} & \ldots & C_{n,n-1} & -1 \end{bmatrix} \qquad \text{(M7)}$$

Here, it can be easily seen that $q_1$ is the first probability from which other probabilities may be computed. It may be beneficial not to start with the probability of the lightest aggregated isotopic variant as a starting probability $q_0$, especially when one only wants to obtain a set of probabilities of aggregated isotopic variants which does not include the lightest mono-isotopic variant. Therefore, in a preferred embodiment, the starting aggregated isotopic variant may comprise the most abundant isotopic variant and/or may be the most-abundant aggregated isotopic variant.

When one wants to obtain only a subset of probabilities $q_i$, it is not always necessary to compute a complete solution of eq. (M5). The skilled reader will appreciate that only that part of a solution for eq. (M5) is required which corresponds to the subset of probabilities $q_i$.

For example for the molecule propane $C_3H_8$, the starting aggregated isotopic variant is the lightest, monoisotopic variant for which the probability is calculated as $q_0 = P(_6^{12}C)^3 \times P(_1^1H)^8$. The next aggregated isotope variant is calculated as $q_1 = q_0 \times \rho_{-1}$, where $\rho_{-1}$ is the first 'negative' power sum of the polynomial $(P(_6^{12}C)I^0 + P(_6^{13}C)I^1)^3 \times (P(_1^1H)I^0 + P(_1^2H)I^1)^8$, which takes the form $$3 \times r_c^{-1} + 8 \times r_H^{-1} \qquad \text{(EL.9)}$$

where $r_c$ and $r_n$ are the root of the terms $(P(_6^{12}C)I^0 + P(_6^{13}C)I^1)$ and $(P(_1^1H)I^0 + P(_1^2H)I^1)$ respectively. Note that the index of the power sum of the roots p indicates the power to which the individual elemental roots are raised. It is already worth mentioning that the complexity of the calculation does not dependent on the values v,w,x,y,z, but on the number of aggregate isotope variants required, which is different from prior art techniques, and which results in an improved, faster, more efficient and more reliable computation and/or analysis of a sample's isotopic distribution.

The roots of the elemental polynomials are trivial and can be stored in the computer memory for further usage. For the elements C, H and N the roots become $$r_C = -\frac{P\binom{12}{6}C}{P\binom{13}{6}C} \quad r_H = -\frac{P\binom{1}{1}H}{P\binom{2}{1}H} \quad r_N = -\frac{P\binom{14}{7}N}{P\binom{15}{7}N} \quad \text{(EL. 10)}$$

The roots of O are complex $r_o$ and complex conjugate $\bar{r}_o$ numbers which take the form $$r_o = \frac{-P\binom{17}{8}O + \sqrt{P\binom{17}{8}O^2 - 4P\binom{16}{8}O P\binom{18}{8}O}}{2P\binom{18}{8}O} \quad \text{(EL. 11)}$$

$$\bar{r}_o = \frac{-P\binom{17}{8}O - \sqrt{P\binom{17}{8}O^2 - 4P\binom{16}{8}O P\binom{18}{8}O}}{2P\binom{18}{8}O}$$

The roots for S are the roots of a fourth-order polynomial and are less trivial, but a closed formed solution exists. The expression looks not very elegant but can be found using the closed form solution or via well-known numerical algorithms. The roots of the sulfur polynomial have two pairs of complex and conjugate roots, namely $(r_{S,1}, \bar{r}_{S,1})$ and $(r_{S,2}, \bar{r}_{S,2})$.

The power sum of the roots (EL.9) in the example above can be expressed more generally. For proteins and peptides this becomes $$\rho_{-d} = vr_C^{-d} + wr_H^{-d} + xr_N^{-d} + yr_O^{-d} + y\bar{r}_O^{-d} + zr_{S,1}^{-d} + zr_{S,1}^{-d} + zr_{S,2}^{-d+\bar{z}}\bar{r}_{S,2}^{-d} \quad \text{(EL.12)}$$

The sum of powers for complex r and conjugate roots $\bar{r}$ can be written as $$r^{-d} + \bar{r}^{-d} = 2|r|^{-d}\cos(-d\phi(r)) \quad \text{(EL.13)}$$

where $|r|$ and $\phi(r)$ indicate the modulus and argument of the roots $r$ and $\bar{r}$ respectively. Given previous formulation (EL.13) the equation (EL.12) can be simplified by replacing the complex and conjugate roots of oxygen and sulfur by its reduced form. For elements with more than four isotopic variants a closed form solution of the roots is often infeasible (Abel-Ruffini theorem), therefore the roots can be calculated by using numerical root finding methods, such as the Newton-Raphson or Dandelin-Graeffe method. The value of $\rho_{-d}$ may be easily calculated using vectorization and recursive formulas for added numbers (e.g. $r_{S,1}^{-d} = r_{S,1}^{-1} r_{S,1}^{-(d-1)}$, so if we have already calculated $\rho_{-(d-1)}$ we may use them to calculate $\rho_{-d}$). In the above text, the powers of the power sum are negative because the above theory calculates the coefficients from the lightest, monoisotopic variant, to heavier variants. In fact, this scheme is the opposite as presented in the Newton-Girard theorem, where the calculation starts with the heaviest variant. Usually information about the heaviest aggregated variants are not required, but if they are necessary the algorithmic method can be parallelized by performing the computation from the lightest variant to the (n/2)'th variant and from the heaviest variant down to the (n/2)'th variant. In the latter part the computation is performed by taking the natural powers instead of the inverse powers as in equation (EL.7).

In addition, we can see that the complexity of calculations depends only on the number of different atoms (in the above text C,H,N,O,S, but obviously this can be extended to all atoms of the periodic system, preferably all atoms of the periodic system which have more than one stable isotope) and does not depend on values of v,w,x,y,z. The method is memory efficient since only two variables, namely, $q_i$ and $\rho_{-d}$, should be stored per required aggregated isotope variant. Hence, calculating the first 100 aggregated isotope variants only requires 201 numbers to be stored.

The computational speed of the outlined method is at least comparable to and in many cases better than the method of Olson and Yergey (Journal of the American Society for Mass Spectrometry 20:295302, 2009) or the method of Rockwood et al. (Analytical Chemistry 68:2027-2030, 1996). However, an extra advantage of the methods of the present invention is on how the center masses of the aggregated isotope variants are calculated. Per definition the center mass $\bar{m}_i$ of the i-th isotope variant is calculated as a probability weighted sum, as discussed by Prouxl and Roussis (Analytical Chemistry 75(6):14701482, 2003):

$$\bar{m}_i = \frac{\Sigma_j m_{ij} p_{ij}}{\Sigma_j p_{ij}} \quad \text{(EL. 14)}$$

where $p_{ij}$ and $m_{ij}$ indicate the probability of occurrence and the mass of the j-th isotope variant contributing to the i-th aggregated isotope variant. It is obvious that accurate computations of the center masses can only be achieved if all the contributing isotope variants are considered, which is difficult and often infeasible due to the combinatorial explosion of the number of isotope variants for large molecules (i.e., the requirement of the Diophantine solution). However, we can try to circumvent this exhaustive calculation by using the Newton-Girard theorem and Viete formulas as proposed earlier. In this case, we would prefer the solution of the following polynomial $$U(I:v,w,x,y,z) = \Sigma_i (\Sigma_j m_{ij} \rho_{ij}) I^i \quad \text{(EL.15)}$$

where the sum over the weighted masses $\Sigma_j m_{ij} p_{ij}$; of the isotope variants with i additional neutrons are the objects of our interest.

It is important to realize that the denominator of equation (EL.14) or, equivalently, the solution of equation (EL.6), is already obtained by the Newton-Girard theorem. In principle, the Newton-Girard algorithm converts the coefficients of the collapsed polynomial (EL.2), i.e., the elemental probabilities $P(_6^{13}C), \ldots, P(_{16}^{36}S)$, into the coefficients of the expanded polynomial (EL.5). It should be noted that this transformation can only be achieved because the occurrence probability of a particular isotope variant is a product of the elemental probabilities composing the isotope variant. Now in the case for mass calculations the implementation of the Newton-Girard principle is less trivial. The mass of an isotope variant is additive in function of the elemental masses composing the isotope variant. Hence, in order to obtain the terms in the numerator of equation (EL.14) or equivalently, the coefficients of polynomial (EL.15), we need to find a shortcut in order to write the addition of terms as a multiplication of terms. To achieve this we use a basic principle from elementary calculus:

$$K^a \times K^b = K^{a+b}. \quad \text{(EL.16)}$$

In order to obtain a formula in the form of polynomial (EL.15), we will introduce an additional indicator variable in polynomial (EL.2):

$$\left(P(^{12}_6C)K^{M(^{12}_6C)}I^0 + P(^{13}_6C)K^{M(^{13}_6C)}I^1\right)^v \times \quad \text{(EL.17)}$$

$$\left(P(^1_1H)K^{M(^1_1H)}I^0 + P(^2_1H)K^{M(^2_1H)}I^1\right)^w \times$$

$$\left(P(^{14}_7N)K^{M(^{14}_7N)}I^0 + P(^{15}_7N)K^{M(^{15}_7N)}I^1\right)^x \times$$

$$\left(P(^{16}_8O)K^{M(^{16}_8O)}I^0 + P(^{17}_8O)K^{M(^{17}_8O)}I^1 + P(^{18}_8O)K^{M(^{18}_8O)}I^2\right)^y \times$$

$$\left(P(^{32}_{16}S)K^{M(^{32}_{16}S)}I^0 + P(^{33}_{16}S)K^{M(^{33}_{16}S)}I^1 + \right.$$

$$\left. P(^{34}_{16}S)K^{M(^{34}_{16}S)}I^2 + P(^{36}_{16}S)K^{M(^{36}_{16}S)}I^4\right)^z,$$

where the indicator variable K acts as a tracking device for the elemental masses $M(^{12}_6C), \ldots, M(^{36}_{16}S)$. Polynomial (EL.17) can now be expressed as a product of the elemental probabilities and the indicator variable K in a similar fashion as in previous part where the probabilities of the isotope variant were calculated:

$$T(I,K;v,w,x,y,z) = \Sigma_i(\Sigma_j p_{ij} K^{m_{ij}})I^i \quad \text{(EL.18)}$$

In the following two steps, we will manipulate the polynomial in (EL.18) in such a way that we obtain the polynomial in equation (EL.15). In the first step we will differentiate the polynomial over K to obtain:

$$\frac{d}{dx}T(I, K; v, w, x, y, z) = \Sigma_i(\Sigma_j m_{ij} p_{ij} K^{m_{ij}-1})I^i \quad \text{(EL. 19)}$$

In the second step, we need to evaluate the indicator variable in equation (EL.19) at a value of 1. By doing so we obtain the polynomial U(I;v,w,x,y,z) as defined in (EL.15).

Now applying the differentiation and evaluation of K at 1 to the collapsed form of polynomial (EL.17) will give $$U(I; v, w, x, y, z) = \quad \text{(EL.20)}$$
$$vQ(I; v-1, w, x, y, z)(P(^{12}_6C)M(^{12}_6C)I^0 + P(^{13}_6C)M(^{13}_6C)I^1) +$$

$$w(I; v, w-1, x, y, z)(P(^1_1H)M(^1_1H)I^0 + P(^2_1H)M(^2_1H)I^1) + \quad \text{(EL.21)}$$

$$x(I; v, w, x-1, y, z)(P(^{14}_7N)M(^{14}_7N)I^0 + P(^{15}_7N)M(^{15}_7N)I^1) + \quad \text{(EL.22)}$$

$$y(I; v, w, x, y-1, z) \quad \text{(EL.23)}$$
$$(P(^{16}_8O)M(^{16}_8O)I^0 + P(^{17}_8O)M(^{17}_8O)I^1 + P(^{18}_8O)M(^{18}_8O)I^2) +$$

$$z(I; v, w, x, y, z-1) \times \quad \text{(EL.24)}$$
$$(P(^{32}_{16}S)M(^{32}_{16}S)I^0 + P(^{33}_{16}S)M(^{33}_{16}S)I^1 + P(^{34}_{16}S)M(^{34}_{16}S)I^2 +$$
$$P(^{36}_{16}S)M(^{36}_{16}S)I^4).$$

Previously we already showed how the coefficients of the expanded polynomial Q can be easily calculated. We only need to modify the algorithm a little bit to account for the extra multiplication with the polynomial containing the weighted elemental masses. Our algorithmic approach will divide the calculations of the polynomial U(I;v,w,x,y,z) in five parts. This means the method iteratively finds coefficients of each of five polynomials (EL.20), (EL.21), (EL.22), (EL.23), (EL.24) starting from the monoisotopic mass; and then add the coefficients with the same order. The final centered masses may be now obtained from equation (EL.14), where the obtained results have to be weighted the occurrence probabilities of the corresponding aggregated isotope variant.

For each power of I (representing the additional nucleon), the above method implicitly solves the Diophantine equation and returns all isotope combinations for which the additional neutron count of the isotope variants sum to the power. Moreover, we are able to adapt the calculation scheme such that mathematical operations on the result of the Diophantine equation were enabled without explicitly calculating the outcome of the diophantine equation.

The skilled person will appreciate that the procedures as described in this document can be applied more broadly to molecules consisting of more different atoms then previously presented. More specifically, the constituting atoms can be any combination of Hydrogen, Helium, Lithium, Beryllium, Boron, Carbon, Nitrogen, Oxygen, Fluorine, Neon, Sodium, Magnesium, Aluminium, Silicon, Phosphorus, Sulfur, Chlorine, Argon, Potassium, Calcium, Scandium, Titanium, Vanadium, Chromium, Manganese, Iron, Cobalt, Nickel, Copper, Zinc, Gallium, Germanium, Arsenic, Selenium, Bromine, Krypton, Rubidium, Strontium, Yttrium, Zirconium, Niobium, Molybdenum, Technetium, Ruthenium, Rhodium, Palladium, Silver, Cadmium, Indium, Tin, Antimony, Tellurium, Iodine, Xenon, Caesium, Barium, Lanthanum, Cerium, Praseodymium, Neodymium, Promethium, Samarium, Europium, Gadolinium, Terbium, Dysprosium, Holmium, Erbium, Thulium, Ytterbium, Lutetium, Hafnium, Tantalum, Tungsten, Rhenium, Osmium, Iridium, Platinum, Gold, Mercury, Thallium, Lead, Bismuth, Polonium, Astatine, Radon, Francium, Radium, Actinium, Thorium, Protactinium, Uranium. More specifically, the aggregated isotope distribution of two molecules which differ in their constituents only by a number of mono-isotopic atoms will look the same, except that the distributions will be displaced in absolute mass. The mono-isotopic atoms, i.e. the atoms with only one stable isotope, are Beryllium-9, Fluorine-19, Sodium-23, Aluminium-27, Phosphorus-31, Scandium-45, Vanadium-51, Manganese-55, Cobalt-59, Arsenic-75, Rubidium-85, Yttrium-89, Niobium-93, Rhodium-103, Indium-113, Iodine-127, Caesium-133, Lanthanum-139, Praseodymium-141, Europium-153, Terbium-159, Holmium-165, Thulium-169, Lutetium-175, Rhenium-185, Gold-197. Furthermore, the specific approach we have postulated suggests a possible reversed calculation for obtaining molecule information based on isotopic distribution information.

The present invention provides a method for analysing at least part of an isotopic distribution of a sample, comprising the following steps at least once:
  providing a chemical formula of a molecule;
  obtaining at least part of an aggregated isotopic distribution of a molecule with a known chemical formula by performing the steps of:
    obtaining data comprising at least one probability $q_j$ with which a j'th aggregated isotopic variant of said molecule with mass number $A_j$ occurs within said aggregated isotopic distribution;
    computing a probability $q_i$ with which an i'th aggregated isotopic variant of said molecule with i>j and with mass number $A_i$ different from $A_j$ occurs within said aggregated isotopic distribution, characterized in that said probability $q_i$ is computed by taking a linear combination of said at least one probability $q_j$ with coefficients $C_{i,j}$, i.e. $q_i = \Sigma_{j=0}^{i-1} C_{i,j} q_j$;
  comparing said aggregated isotopic distribution as obtained in the previous step, with said isotopic distribution of said sample to analyse said sample for the presence of said molecule.

The benefit of the above approach is that not all isotopic variants need to be computed, leading to a faster computation of the aggregated isotopic distribution. Furthermore, prior art methods may have needed to compute factorials of large numbers, which computationally can become very difficult and possibly inaccurate, and which consequently led to large computation or data-retrieval times in a trial-and-error method for analysing the isotopic distribution of a sample. This is not the case in the method described in this document. The exact values of the coefficients $C_{i,j}$ depends on which probabilities $q_j$ are known, on which probability $q_i$ is desired, and obviously on the chemical formula of the molecule, i.e. once all $q_j$'s are known and the chemical formula is known, the coefficients $C_{i,j}$ for computing a specified $q_i$ are unique. However, no elaborate computations are involved and the coefficients $C_{i,j}$ can be easily obtained using e.g. one of the algorithms described in this text. Also, the data comprising at least one probability $q_j$ with which a j'th aggregated isotopic variant of said molecule with mass number $A_j$ occurs within said aggregated isotopic distribution, can be obtained in a number of ways, via computation according to known techniques or via a lookup in a database comprising a listing of probabilities and/or mass numbers of isotopic and/or aggregated isotopic variants of a set of molecules.

In an embodiment, said one or more probabilities $q_j$ are obtained by performing the steps of:
  obtaining a probability $q_0$ with which a starting aggregated isotopic variant of said molecule with mass number $A_0$ occurs in said aggregated isotopic distribution;
  recursively computing probabilities $q_j$ for j>0 by taking linear combinations of said probability $q_0$ and previously computed probabilities $q_{j'}$ with j'<j and with coefficients $C_{j,j'}$, i.e. $q_j = \Sigma_{j'=0}^{j-1} C_{j,j'} q_{j'}$.

This means that the probabilities $q_j$ are themselves computed using the same method as the probability $q_i$, which leads to a recursive computation of the aggregated isotopic distribution, beginning with a starting probability $q_0$ with which the aggregated isotopic variant with mass number $A_0$ occurs in the aggregated isotopic distribution. The starting point can be chosen in function of the purpose of the computation of the aggregated isotopic distribution, i.e. it may be chosen such that it is easy to compute $q_0$, or it may be chosen such that the coefficients $C_{i,j}$, are easy to compute, or the starting aggregated isotopic variant may comprise the most abundant isotopic variant, or the starting aggregated isotopic variant may be the most abundant aggregated isotopic variant, etc.

In a preferred embodiment, the first aggregated isotopic variant of said molecule is a mono-isotopic variant. In this case the starting probability $q_0$ is easily computed as the product of the abundances of the isotopes of the atoms which constitute the molecule. In a more preferred embodiment, the first aggregated isotopic variant is the lightest isotopic variant. In another more preferred embodiment, the first aggregated isotopic variant is the heaviest isotopic variant. The lightest and the heaviest aggregated isotopic variants of a molecule are mono-isotopic since they consist of only the lightest or only the heaviest isotopes of the constituting atoms respectively. Thus, if the chemical formula of the molecule is described by $\Pi_\alpha (Z_\alpha)_{n_\alpha}$ with
  $\alpha$ an index running over all constituent atomic species of the molecule;
  $Z_\alpha$ the $\alpha$'th atomic species of the molecule; and
  $n_\alpha$ the number of atoms of species $Z_\alpha$ in the molecule,
and atomic species $Z_\alpha$ has isotopes $P(_{Z_\alpha}^{A_\alpha+m_\alpha}Z_\alpha)$ with $A_\alpha$ the mass number of the lightest isotope of atomic species $Z_\alpha$ and $m_\alpha$ the extra neutron content of the isotopes of atomic species $Z_\alpha$, then the probability with which the lightest aggregated isotopic variant of the molecule occurs is given by the product of the abundances of the lightest isotopes of the constituting atoms: $q_0 = \Pi_\alpha [P(_{Z_\alpha}^{A_\alpha}Z_\alpha)]^{n_\alpha}$. Similarly, the probability with which the heaviest aggregated isotopic variant of the molecule occurs is given by the product of the abundances of the heaviest isotopes of the constituting atoms: $q_0 = \Pi_\alpha [P(_{Z_\alpha}^{A_\alpha+N_\alpha}Z_\alpha)]^{n_\alpha}$ when the heaviest isotope of atomic species $Z_\alpha$ has $N_\alpha$ neutrons more than the lightest isotope, i.e. atomic species $Z_\alpha$ has at most $N_\alpha+1$ stable isotopes. Note that the index '0' is used to denote the starting aggregated isotopic variant, rather than e.g. the lightest. The number of isotopic variants of the molecule is further given by $1+n=1+\Sigma_\alpha N_\alpha n_\alpha$. In an even more preferred embodiment, the probabilities $q_i$ for the $$\binom{n}{2}$$

lightest aggregated isotopic variants are computed recursively starting from the probability for the lightest aggregated isotopic variant and the probabilities $q_i$ for (n/2) heaviest aggregated isotopic variants are computed recursively starting from the probability for the heaviest aggregated isotopic variant.

If the probability $q_0$ is known, the subsequent probabilities $q_i$ with which the i'th aggregated isotopic variant with mass number $A_i$ occurs, can be computed, preferably recursively, using the formula $$q_i = \Sigma_{j=0}^{i-1} C_{i,j} q_j \qquad (1)$$

i.e. the probability $q_i$ is computed by taking a linear combination of probabilities $q_j$ with which aggregated isotopic variants of the molecule with mass numbers $A_j$ occur, whereby these probabilities $q_j$ were previously obtained, preferably recursively by a method as described in this document.

When the molecule has the chemical formula $\Pi_\alpha (Z_\alpha)_{n_\alpha}$ as described above, the coefficients $C_{i,j}$ in the previously discussed methods can be obtained by using the steps of:
  obtaining for each value of $\alpha$, each root $r_{\alpha,i_\alpha}$, with $i_\alpha = 1 \ldots N_\alpha$, of an $N_\alpha$'th order elemental polynomial equation whose coefficient of the $m_\alpha$'th order term is given by an elemental abundance $P(_{Z_\alpha}^{A_\alpha+m_\alpha}Z_\alpha)$ of an isotope of the atomic species $Z_\alpha$ with $m_\alpha$ neutrons more than the lightest, preferably stable, isotope of said atomic species which has atomic mass number $A_\alpha$, i.e. $A_\alpha$ is the mass number of the lightest isotope of said atomic species;
  computing said coefficients $C_{i,j}$ from said roots $r_{\alpha,i_\alpha}$.

For each value of $\alpha$, i.e. for each atomic species $Z_\alpha$, an elemental polynomial equation can be constructed:

$$\Sigma_{m_\alpha=0}^{N_\alpha} P(_{Z_\alpha}^{A_\alpha+m_\alpha}Z_\alpha) r^{m_\alpha} = 0 \qquad (EL.25)$$

Here, $P(_{Z_\alpha}^{A_\alpha+m_\alpha}Z_\alpha)$ is the elemental abundance of an isotope of the atomic species $Z_\alpha$ with $m_\alpha$ neutrons more than the lightest stable isotope of said atomic species which has atomic mass number $A_\alpha$. The polynomial equation in I (EL.25) has $N_\alpha$ roots $r_{\alpha,i_\alpha}$, with $i_\alpha = 1 \ldots N_\alpha$. These roots may be complex, depending on the values of the abundances $P(_{Z_\alpha}^{A_\alpha+m_\alpha}Z_\alpha)$. The roots $r_{\alpha,i_\alpha}$ for the different atomic species $Z_\alpha$ constituting the molecule can be easily obtained by retrieval from a database or computed and stored. These roots can be used in the computation of the coefficients $C_{i,j}$ using e.g. the Newton-Girard theorem and Viete's formulas (see e.g. I. G. Macdonald, "Symmetric functions and Hall polynomials", Clarendon Press, Oxford University Press, Oxford: New York, 1979). In other words we assume that the elements of the molecule occur with known abundances, herein called elemental abundances. It should be clear that the method of the present invention can be used when the elemental abundances are as they appear in nature, e.g. as quoted in K. J. R. Rosman and P. D. P. Taylor, "Isotopic composition of the elements 1997", Pure and Applied Chemistry 70(1):217-235, 1988, as long as the elemental abundances are known and/or postulated for the sample, e.g. the elemental abundances to be used for a sample collected at high altitude, where there can be a lot of radiation, may be different than the elemental abundances to be used for a sample collected in the ocean or on the ground. If the sample is biological, one may e.g. assume that the elemental abundances of the elements C, N, H, O, S are as listed in table (ELT.1).

In an embodiment where the starting aggregated isotopic variant is the lightest isotopic variant the coefficients of the linear combination of eq. (1) are given by $$C_{i,j} = -\frac{1}{i}\rho_{-(i-j)} \qquad (2a)$$

In this case $C_{i,j}$ can be given in terms of $\rho_d$ which are power sums of the roots of well-known elemental polynomial equations (see later).

In an embodiment where the starting aggregated isotopic variant is the heaviest isotopic variant the coefficients of the linear combination of eq. (1) are given by $$C_{i,j} = -\frac{1}{i}\rho_{(i-j)} \qquad (2b)$$

In this case $C_{i,j}$ can be given in terms of $\rho_d$ which are power sums of the roots of well-known elemental polynomial equations (see later).

In the previous paragraphs, the coefficients of the linear combination $C_{i,j}$ in eqs. (2a) and (2b) are expressed in terms of power sums $\rho_d$ of the roots of certain well-known elemental polynomial equations (EL.25). In case the molecule's chemical formula is given by $\Pi_\alpha(Z_\alpha)_{n_\alpha}$ whereby $Z_1, Z_2, \ldots, Z_y$ are the molecule's constituent atomic species, with y the number of different atomic species constituting the molecule, $$P\binom{A_1}{Z_1}Z_1)I^0 + P\binom{A_1+1}{Z_1}Z_1)I^1 + \ldots + P\binom{A_1+N_1}{Z_1}Z_1)I^{N_1} = 0 \qquad (3a)$$

$$P\binom{A_2}{Z_2}Z_2)I^0 + P\binom{A_2+1}{Z_2}Z_2)I^1 + \ldots + P\binom{A_2+N_2}{Z_2}Z_2)I^{N_2} = 0 \qquad (3b)$$

$$\ldots$$

$$P\binom{A_y}{Z_y}Z_y)I^0 + P\binom{A_y+1}{Z_y}Z_y)I^1 + \ldots + P\binom{A_y+N_y}{Z_y}Z_y)I^{N_y} = 0 \qquad (3c)$$

Here, I is the unknown variable which may represent the number of surplus neutrons in the isotopic variants as compared to the lightest stable isotopic invariant; $A_1, A_2, \ldots, A_y$ may be mass numbers of the lightest stable isotopic variant of atom species $Z_1, Z_2, \ldots, Z_y$ respectively; $N_1, N_2, \ldots, N_y$ may represent the maximum number of surplus neutrons which can be added to the lightest isotopic variant of atomic species $Z_1, Z_2, \ldots, Z_y$ respectively to get the heaviest stable isotopic variant. The coefficients $P(_{Z_1}{}^{A_1+i}Z_1)$, $P(_{Z_2}{}^{A_2+j}Z_2)$, ..., $P(_{Z_y}{}^{A_y+k}Z_y)$ of the polynomial equations are the elemental abundances of the isotopes of atom species $Z_1, Z_2, \ldots, Z_y$ with mass numbers $A_1+i, A_2+j, \ldots, A_y+k$ respectively. The solutions of eqs. (3a)-(3c) are a set of $N_1+N_2+\ldots+N_y$ roots $(r_{1,1}, r_{1,2}, \ldots, r_{1,N_1}; r_{2,1}, r_{2,2}, \ldots r_{2,N_2}; \ldots; r_{y,1}, r_{y,2}, \ldots, r_{r,N_y})$ which may be complex numbers. The numbers $\rho_d$ for constructing the coefficients $C_{i,j}$ in the linear combination of eq. (1) are the power sums of these roots, more specifically:

$$\rho_d = \sum_{\alpha=1}^{y} n_\alpha \sum_{i_\alpha}^{N_\alpha} r_{\alpha,i_\alpha}^d \qquad (4)$$

$$= n_1(r_{1,1}^d + r_{1,2}^d + \ldots + r_{1,N_1}^d) + n_2(r_{2,1}^d + r_{2,2}^d + \ldots + r_{2,N_2}^d) + \ldots +$$
$$n_y(r_{y,1}^d + r_{y,2}^d + \ldots + r_{y,N_y}^d)$$

In an embodiment where the starting aggregated isotopic variant of a molecule with pre-determined mass number $A_0$ is the lightest, and therefore mono-isotopic, variant, the power d is negative and the coefficients of the linear combination of eq. (1) may depend on the negative power sums $\rho_{-2}$, $\rho_{-2}, \ldots, \rho_{-(i-1)}$ as in eq. (2a). In an embodiment where the starting aggregated isotopic variant of a molecule with pre-determined mass number $A_0$ is the heaviest, and therefore mono-isotopic, variant, the power d is positive and the coefficients of the linear combination of eq. (1) may depend on the positive power sums $\rho_1, \rho_2, \ldots, \rho_{(i-1)}$ as in eq. (2b).

In embodiments where the probabilities $q_i$ are computed recursively, one may compute the starting probability $q_0$ according to any prior art technique or, as indicated before, one may also obtain $q_0$ from a database. One may then compute $q_1$ from $q_0$, then one can compute $q_2$ as a linear combination of $q_0$ and $q_1$, etc., using the coefficients $C_{i,j}$. In the case of a recursive computation of the $q_i$ with $i>0$, the subsequent power sums $\rho_d$, e.g. with $d=-i$, which are used in the computation of the coefficients $C_{i,j}$ can be computed using previously computed power sums. Therefore, in an embodiment, said starting aggregated isotopic variant is the lightest isotopic variant and said coefficients $C_{i,j}$ are computed according to $$C_{i,j} = -\frac{1}{i}\sum_\alpha n_\alpha \sum_{i_\alpha} r_{\alpha,i_\alpha}^{-(i-j)}.$$

In a preferred embodiment, the powers of roots $r_{\alpha,i_\alpha}^{-(i-j)}$ in the computation of said coefficients $C_{i,j}$ are computed recursively.

In an embodiment, the invention provides a method for analysing at least part of an isotopic distribution of a sample, whereby said chemical formula is described by $\Pi_\alpha(Z_\alpha)_{n_\alpha}$ with α an index running over all constituent atomic species of the molecule;

$Z_\alpha$ the α'th atomic species of the molecule; and $n_\alpha$ the number of atoms of species $Z_\alpha$ in the molecule, and whereby the method further comprises the steps of:

generating data comprising weighted average masses $p_i{}^\alpha$ of each atomic species $Z_\alpha$ within said i'th aggregated isotopic variant of said molecule with mass number $A_i$;

computing a center mass $M_i$ of said i'th aggregated isotopic variant of said molecule from said weighted average masses $p_i{}^\alpha$ of each atomic species $Z_\alpha$ and from said probability $q_i$.

In a preferred embodiment, said center mass $M_i$ is computed according to:

$$M_i = \frac{1}{q_i}\sum_\alpha n_\alpha p_i^\alpha, \qquad (5)$$

The weighted average masses $p_i^\alpha$ are the relative contribution of atomic species $Z_\alpha$ to the mass of the i'th aggregated isotopic variant, normalized to the probability $q_i$. In other words, $p_i^\alpha$ is the mass contribution of 1 atom of species $Z_\alpha$ to the mass $M_i$ of the i'th aggregated isotopic variant, weighted by the relative probabilities with which the different isotopes of the atomic species occur in the i'th aggregated isotopic variant, these relative probabilities being normalized to the probability $q_i$ with which the i'th aggregated isotopic variant occurs in the aggregated isotopic distribution. A simple example may explain better the meaning of $p_i^\alpha$. We refer to example 2 for this explanation.

The generation of data comprising center masses of aggregated isotopic variants of a molecule may be done along similar lines as the generation of the probabilities with which aggregated isotopic variants of a molecule occur in an aggregated isotopic distribution. The center mass $M_i$ of the i'th aggregated isotopic variant of a molecule is defined by:

$$M_i = \frac{\sum_j M_{i,j} p_{i,j}}{\sum_j p_{i,j}} \quad (5a)$$

with $M_{i,j}$ the mass of the j'th contributing isotopic variant to the i'th aggregated isotopic variant of the molecule, and $p_{i,j}$ the probability with which an isotopic variant (note that this is not an aggregated isotopic variant) contributes to the isotopic distribution of the molecule, and whereby the sum over j runs over all isotopic variants contributing to the i'th aggregated isotopic variant. Remark that the denominator in eq. (5a): $\Sigma_j p_{i,j} = q_i$, whereby $q_i$ is the probability with which the i'th aggregated isotopic variant of said molecule with mass number $A_i$ occurs in the molecule's aggregated isotopic distribution. Note that eq. (5a) is the same as eq. (EL.14) for $M_i = \overline{m}_i$ and $M_{i,j} = m_{i,j}$.

In case the starting aggregated isotopic variant is a mono-isotopic variant, the center mass $M_0$ of the starting aggregated isotopic variant of the molecule with pre-determined mass number $A_0$ is given by the sum of the masses of those isotopes of the constituent atoms which contribute to said starting aggregated isotopic variant. In case the starting aggregated isotopic variant is the lightest isotopic variant, the center mass $M_0$ of the starting aggregated isotopic variant of the molecule with pre-determined mass number $A_0$ is given by the sum of the masses of the lightest isotopes of the constituent atoms. In case the starting aggregated isotopic variant is the heaviest isotopic variant, the center mass $M_0$ of the starting aggregated isotopic variant of the molecule with pre-determined mass number $A_0$ is given by the sum of the masses of the heaviest isotopes of the constituent atoms. Although it is possible to choose any aggregated isotopic variant as a starting aggregated isotopic variant for which the center mass $M_0$ is to be generated, it is easier to choose a mono-isotopic variant, since this requires less computation and/or data-retrieving time. Note that in the above, the index '0' was used to denote the starting aggregated isotopic variant, and not necessarily e.g. the lightest.

In an embodiment where a center mass is computed, at least one weighted average mass $p_i^\alpha$ is computed by taking a linear combination of weighted average masses $p_j^\alpha$ of atomic species $Z_\alpha$ within aggregated isotopic variants of said molecule with mass numbers $A_j$ different from $A_i$, i.e. $p_i^\alpha = \Sigma_{j=0}^{i-1} D_{i,j}^\alpha p_j^\alpha$ with $D_{i,j}^\alpha$ the coefficients of the linear combination. The benefits of this approach for computing the center mass of the i'th aggregated isotopic variant along these lines is that no information on the separate isotopic variant contributing to the i'th aggregated isotopic variant is needed or needs to be computed, thereby saving on computing or data-retrieval time as compared to prior art techniques. The weighted average mass $p_i^\alpha$ for an atomic species $Z_\alpha$ and the i'th aggregated isotopic variant can be computed from the weighted average masses $p_j^\alpha$ of the same atomic species $Z_\alpha$ and of other aggregated isotopic variants with index $j \neq i$, which can be obtained from a database, computed according to a prior art technique, computed from first principles, computed according to any technique specified in this document or any other technique. The exact values of the coefficients $D_{i,j}^\alpha$ depend on indices $i, j, \alpha$ and on the molecule's chemical formula, but are unique, i.e. if the weighted average masses $p_j^\alpha$ for aggregated isotopic variants with mass numbers $A_j \neq A_i$ and for atomic species $Z_\alpha$ are known, the coefficients $D_{i,j}^\alpha$ for computing the weighted average mass $p_i^\alpha$ are uniquely determined. In a preferred embodiment, said weighted average mass $p_i^\alpha$ is computed recursively starting from a weighted average mass $p_0^\alpha$ of each atomic species $Z_\alpha$ within a zeroth or starting aggregated isotopic variant of said molecule with mass number $A_0$. In such an embodiment, the center masses of one or more aggregated isotopic variants can be more accurately and more quickly computed than with prior art techniques. Furthermore, computing the weighted average masses recursively reduces the need of consulting databases, hereby possibly reducing computing time. In a preferred embodiment, a coefficient $D_{i,j}^\alpha$ for a pre-determined value of $\alpha$ is obtained using the steps of:

obtaining for each value of $\alpha$, each root $r_{\alpha, i_\alpha}$, with $i_\alpha = 1 \ldots N_\alpha$, of an $N_\alpha$'th-order elemental polynomial equation whose coefficient of the $m_\alpha$'th order term is given by an elemental abundance $P(_{Z_\alpha}^{A_\alpha + m_\alpha} Z_\alpha)$ of the isotope of atomic species $Z_\alpha$ with $m_\alpha$ neutrons more than the lightest stable isotope of said atomic species which has atomic mass number $A_\alpha$;

obtaining for said pre-determined value of $\alpha$, each root $s_{\alpha, i_\alpha}$, with $i_\alpha = 1 \ldots N_\alpha$, of an $N_\alpha$'th-order extended polynomial equation whose coefficient of the $m_\alpha$'th-order term is given by the product of an elemental abundance $P(_{Z_\alpha}^{A_\alpha + m_\alpha} Z_\alpha)$ and the mass $M(_{Z_\alpha}^{A_\alpha + m_\alpha} Z_\alpha)$ of the isotope of atomic species $Z_\alpha$ with $m_\alpha$ neutrons more than the lightest stable isotope of said atomic species which has atomic mass number $A_\alpha$;

computing said coefficient $D_{i,j}^\alpha$ from said roots $r_{\alpha, i_\alpha}$ and $s_{\alpha, i_\alpha}$.

The elemental polynomial equations and the roots $r_{\alpha, i_\alpha}$, have already been discussed above, e.g. in eqs. (EL.25), (3a), (3b) and (3c) and in the text. The extended polynomial equations use the masses of the isotopes of the constituting atomic species. More in particular, the polynomial equations can be written as:

$$\Sigma_{m_\alpha = 0}^{N_\alpha} M(_{Z_\alpha}^{A_\alpha + m_\alpha} Z_\alpha) P(_{Z_\alpha}^{A_\alpha + m_\alpha} Z_\alpha) I^{m_\alpha} = 0 \quad (6)$$

in case the molecule's chemical formula is given by $\Pi_\alpha (Z_\alpha)_{n_\alpha}$ whereby $Z_1, Z_2, \ldots, Z_y$ are the molecule's constituent atomic species, with y the number of different atomic species constituting the molecule. The extended polynomial equations look like:

$$M(_{Z_1}^{A_1} Z_1) P(_{Z_1}^{A_1} Z_1) I^0 + \quad (7a)$$
$$M(_{Z_1}^{A_1+1} Z_1) P(_{Z_1}^{A_1+1} Z_1) I^1 + \ldots + M(_{Z_1}^{A_1+N_1} Z_1) P(_{Z_1}^{A_1+N_1} Z_1) I^{N_1} = 0$$

-continued $$M(^{A_2}_{Z_2}Z_2)P(^{A_2}_{Z_2}Z_2)I^0 + \quad (7b)$$
$$M(^{A_2+1}_{Z_2}Z_2)P(^{A_2+1}_{Z_2}Z_2)I^1 + \ldots + M(^{A_2+N_2}_{Z_2}Z_2)P(^{A_2+N_2}_{Z_2}Z_2)I^{N_2} = 0$$
$$\ldots$$

$$M(^{A_y}_{Z_y}Z_y)P(^{A_y}_{Z_y}Z_y)I^0 + \quad (7c)$$
$$M(^{A_y+1}_{Z_y}Z_y)P(^{A_y+1}_{Z_y}Z_y)I^1 + \ldots + M(^{A_y+N_y}_{Z_y}Z_y)P(^{A_y+N_y}_{Z_y}Z_y)I^{N_y} = 0$$

Here, I is the unknown variable which may represent the number of surplus neutrons in the isotopic variants as compared to the lightest stable isotopic invariant; $A_1, A_2, \ldots, A_y$ may be mass numbers of the lightest stable isotopic variant of atom species $Z_1, Z_2, \ldots, Z_y$, respectively; $N_1, N_2, \ldots, N_y$ may represent the maximum number of surplus neutrons which can be added to the lightest isotopic variant of atomic species $Z_1, Z_2, \ldots, Z_y$ respectively to get the heaviest stable isotopic variant. The coefficients $M(_{Z_1}{}^{A_1+i}Z_1)P(_{Z_1}{}^{A_1+i}Z_1)$, $M(_{Z_2}{}^{A_2+j}Z_2)P(_{Z_2}{}^{A_2+j}Z_2)$, $\ldots$, $M(_{Z_y}{}^{A_y+k}Z_y)P(_{Z_y}{}^{A_y+k}Z_y)$ of the polynomial equations are products of the elemental abundances and the masses of the isotopes of atom species $Z_1, Z_2, \ldots, Z_y$ with mass numbers $A_1+i, A_2+j, \ldots, A_y+k$ respectively. The solutions of eqs. (7a)-(7c) are a set of $N_1+N_2+\ldots+N_y$ roots $(s_{1,1}, s_{1,2}, \ldots, s_{1,N_1}; s_{2,1}, s_{2,2}, \ldots, s_{2,N_2}; \ldots; s_{y,1}, s_{y,2}, \ldots, s_{y,N_y})$ which may be complex numbers. In a more preferred embodiment, said zeroth or starting aggregated isotopic variant of said molecule is the lightest isotopic variant, and said coefficients $D_{i,j}{}^\alpha$ are computed according to $$D_{i,j}^\alpha = -\frac{1}{i}\left[\sum_{\alpha'}\left(n_{\alpha'}\sum_{i_{\alpha'}}r_{\alpha',i_{\alpha'}}^{-(i-j)}\right) - r_{\alpha,i_\alpha}^{-(i-j)} + s_{\alpha,i_\alpha}^{-(i-j)}\right] \quad (8)$$

where $\alpha'$ is an index which runs over all atomic species constituting the molecule, i.e. $\alpha'=1 \ldots y$. In another more preferred embodiment, said zeroth aggregated isotopic variant of said molecule is the heaviest isotopic variant and the coefficients $D_{i,j}{}^\alpha$ are computed as a sum of positive powers of the roots of the elemental and extended polynomial equations.

In an embodiment, the center masses $M_i$ for the $$\binom{n}{2}$$

lightest aggregated isotopic variants are computed recursively starting from the lightest aggregated isotopic variant and the center masses $M_i$ for the $$\binom{n}{2}$$

heaviest aggregated isotopic variants are computed recursively starting from the probability for the heaviest aggregated isotopic variant. The coefficients $D_{i,j}{}^\alpha$ are in this case computed according to eq. (8) for the $$\binom{n}{2}$$

lightest aggregated isotopic variants and as a sum of positive powers of the roots of the elemental and extended polynomial equations for the $$\binom{n}{2}$$

heaviest aggregated isotopic variants.

In a preferred embodiment, the powers of said roots $r_{\alpha,i_\alpha}^{-(i-j)}$ and/or $s_{\alpha,i_\alpha}^{-(i-j)}$ in the computation of said coefficients $D_{i,j}{}^\alpha$ are computed recursively, i.e. in a recursive computation, the $(i-j-1)$'th negative power of said roots has already been obtained and can be stored for further usage when computing the $(i-j)$'th negative power: $r_{\alpha,i_\alpha}^{-(i-j)} = r_{\alpha,i_\alpha}^{-(i-j-1)}r_{\alpha,i_\alpha}^{-1}$ and $s_{\alpha,i_\alpha}^{-(i-j)} = s_{\alpha,i_\alpha}^{-(i-j-1)}s_{\alpha,i_\alpha}^{-1}$. It is clear that such a procedure reduces computing time considerably for large powers.

In a further aspect, the present invention provides a device capable of analysing at least part of an isotopic distribution of a sample and/or of a molecule in a sample, using a method for analysing at least part of an isotopic distribution of a sample as described in this document. This includes, but is not limited to a computer and a mass spectrometer.

In yet another aspect, the present invention provides a computer-mountable device comprising an implementation of a method for analysing at least part of an isotopic distribution of a sample as described in this document. Such a computer-mountable device can be a hard disk, a floppy disk, a USB stick or other kind of flash-memory, an internet connection to a database or website where an implementation of such a method is available.

In still another aspect, the present invention provides a use of a method for analysing at least part of an isotopic distribution of a sample as described in this document, preferably on a computer and/or a mass spectrometer and/or a peripheral instrument of a mass spectrometer and/or any other apparatus.

As shown in FIG. 2, in a further aspect, the present invention provides a method for identifying the elemental composition of and/or quantifying the presence of mono-isotopic elements in a molecule in a sample, whereby said molecule has a chemical formula $\Pi_\alpha (Z_\alpha)n_\alpha$ with $\alpha$ an index running over a number of expected constituent atomic species of said molecule;

$Z_\alpha$ the $\alpha$'th expected atomic species of the molecule; and $n_\alpha$ the number of atoms of species $Z_\alpha$ in the molecule, comprising the steps of:

obtaining at least a part of an isotopic distribution from said sample;

obtaining a set of $N_p$ peak heights $t_j$ with $j=1 \ldots N_p$, of at least part of an aggregated isotopic distribution from said isotopic distribution;

computing from said set of peak heights a set of $N_p-1$ relative peak heights $\{\hat{t}\}_i$ with $i=1 \ldots N_p-1$;

obtaining a value of $n_\alpha$ for at least one atomic species $Z_\alpha$ from said set of relative peak heights, characterized in that said value of $n_\alpha$ is obtained by computing a solution of a system of linear equations $E_\alpha E_{i\alpha} n_\alpha = F_i$, preferably this solution may be rounded to the nearest integers or the solution may be computed using a discrete optimization algorithm, whereby the set of numbers $F_i$ comprises said set of relative peak heights and the coefficients $E_{i\alpha}$ of said linear system comprise powers and/or power sums of roots $r_{\alpha,i_\alpha}$, with $i_\alpha=1 \ldots N_\alpha$, of an $N_\alpha$'th-order elemental polynomial equation whose coefficient of the $m_\alpha$'th order term is given by an elemental abundance $P(_{Z_\alpha}^{A_\alpha+m_\alpha}Z_\alpha)$ of the isotope of the atom species $Z_\alpha$ with ma neutrons more than the lightest stable isotope of said atom species which has atomic mass number $A_\alpha$. It should be clear that obtaining at least one value of $n_\alpha$ for at least one atomic species $Z_\alpha$ in the above-prescribed way drastically reduces the time for identifying the elemental composition of and/or quantifying the presence of mono-isotopic elements in a molecule in a sample, since no trial-and-error or fitting method as in the prior art is used for obtaining this $n_\alpha$, whereby a guess was made as to the value of $n_\alpha$, the (aggregated) isotopic distribution for this guess-value had to be computed or retrieved from a database and subsequently compared to the obtained isotopic distribution from the sample, after which another guess for $n_\alpha$ was tried and tested. Therefore, the method of the present invention is a clear improvement over prior art methods, e.g. the methods disclosed in the documents which were discussed previously.

In an embodiment, in the method for identifying the elemental composition of and/or quantifying the presence of mono-isotopic elements in a molecule in a sample, said set of peak heights $t_j$ is ordered according to the mass at which a peak height is observed. This makes the computation of the coefficients $E_{i\alpha}$ easier and more straightforward. In a preferred embodiment, no peak is observed in said isotopic distribution or said aggregated isotopic distribution around a mass which is essentially 1 Da smaller than the mass at which the first of said set of peak heights $t_j$, i.e. $t_1$, is observed. Again, this makes the computation of the coefficients $E_{i\alpha}$, easier and more straightforward. In a preferred embodiment, the masses at which the peak heights $t_j$ are observed are essentially 1 Da apart. Also this makes the computation of the coefficients $E_{i\alpha}$ easier and more straightforward.

In an embodiment of the method for identifying the elemental composition of and/or quantifying the presence of mono-isotopic elements in a molecule in a sample, said set of $N_p-1$ relative peak heights $\hat{t}_i$ with $i=1 \ldots N_p-1$ is computed recursively from said set of $N_p$ peak heights $t_i$ with $j=1 \ldots N_p$, using the steps of:

$$\text{computing } \hat{t}_1 = -\frac{t_2}{t_1}; \quad (9a)$$

$$\text{computing } \hat{t}_{i+1} = -\frac{1}{t_1}\left[(i+1)t_{i+2} + \sum_{j=1}^{i}\hat{t}_{i-j+1}t_{j+1}\right] \quad (9b)$$

for $i = 2 \ldots N_p - 1$.

As such, one can easily, quickly and accurately compute normalized peak heights which are directly comparable to the probabilities $q_i$ normalized to a probability $q_j$ corresponding to peak $t_1$, i.e. the peak $t_1$ is observed at mass number $A_j$ to which a $q_j$ corresponds. Furthermore, it should be noted that the ratio $t_1/q_j$ is a measure for the quantity of the molecule in the sample, i.e. from the value of $t_1/q_j$, one may derive the amount of the molecule in the sample. In a preferred embodiment, said coefficients $E_{i\alpha}$ of said linear system are given by the sum of the $(-i)$'th power of the $N_\alpha$ roots of the $N_\alpha$'th-order elemental polynomial equation whose coefficient of the $m_\alpha$'th-order term is given by the elemental abundance $P(_{Z_\alpha}^{A_\alpha+m_\alpha}Z_\alpha)$ of the isotope of atomic species $Z_\alpha$ with $m_\alpha$ neutrons more than the lightest stable isotope of said atomic species which has atomic mass number $A_\alpha$, i.e. $E_{i\alpha} = \Sigma_{i_q=1}^{N_\alpha} r_{\alpha,i_\alpha}^{-i}$, and whereby said set of numbers $F_i$ is given by said set of relative peak heights $\hat{t}_i$, i.e. $F_i = \hat{t}_i$. This embodiment allows for a computation of $n_\alpha$ for at least one and possibly all atomic species $Z_\alpha$, without the necessity of consulting an exterior database, i.e. all which is needed is the set of peak heights $t_j$ with $j=1 \ldots N_p$, of at least part of an aggregated isotopic distribution from an obtained isotopic distribution of a sample.

In an embodiment of the method for identifying the elemental composition of and/or quantifying the presence of mono-isotopic elements in a molecule in a sample, said number $N_p-1$ of relative peaks heights is at least said number y of expected constituent atomic species of said molecule with two or more stable isotopes. As such, one has the possibility of computing the values $n_\alpha$ for all atomic species using the quick and accurate techniques described in this document.

In an embodiment of the method for identifying the elemental composition of and/or quantifying the presence of mono-isotopic elements in a molecule in a sample, said number $N_p-1$ of relative peaks heights is greater than the number of expected constituent atomic species of said molecule with two or more stable isotopes and values for $n_\alpha$ for each value of $\alpha$ are obtained by solving an over-determined system of linear equations $\Sigma_\alpha E_{i\alpha}n_\alpha = F_i$. This solution can be obtained by any prior art technique, e.g. by using a least-square solving algorithm and preferably a subsequent rounding of the resulting solutions to the nearest integers. The latter technique offers the possibility of estimating the error on the obtained solutions for the values of $n_\alpha$.

In an embodiment of the method for identifying the elemental composition of and/or quantifying the presence of mono-isotopic elements in a molecule in a sample, said part of an isotopic distribution is provided by analysis of a mass spectrometric measurement. Mass spectrometric measurements are by far the most popular way of obtaining an isotopic distribution of a sample. The presented method can be used in the analysis of the composition of a sample via mass spectrometry. Since the presented method is in many cases faster, more accurate and more reliable than existing techniques for identifying the elemental composition of and/or quantifying the presence of mono-isotopic elements in a molecule in a sample, it is a major improvement over prior art techniques, especially if the sample consists of large molecules. The method can also serve as an additional quality metric, whereby the estimate for the elemental composition can be compared to the outcome of a Sequest or Mascot database search for peptide identification. Large molecules are typically found in biological samples. Therefore, in an embodiment, said sample comprises polypeptide molecules. Since these polypeptide molecules consist largely of a small set of chemical elements and the presented method for identifying the elemental composition of and/or quantifying the presence of mono-isotopic elements in a molecule in a sample still requires a choice as to which atomic species can be found in the sample, in an embodiment of the method for identifying the elemental composition of and/or quantifying the presence of mono-isotopic elements in a molecule in a sample, said expected atomic species comprise carbon, hydrogen, nitrogen, oxygen and/or sulfur. In an embodiment of the method for identifying the elemental composition of and/or quantifying the presence of mono-isotopic elements in a molecule in a sample, said expected atomic species comprise Hydrogen, Helium, Lithium, Beryllium, Boron, Carbon, Nitrogen, Oxygen, Fluorine, Neon, Sodium, Magnesium, Aluminium, Silicon, Phosphorus, Sulfur, Chlorine, Argon, Potassium, Calcium, Scandium, Titanium, Vanadium, Chromium, Manganese, Iron, Cobalt, Nickel, Copper, Zinc, Gallium, Germanium, Arsenic, Selenium, Bromine, Krypton, Rubidium, Strontium, Yttrium, Zirconium, Niobium, Molybdenum, Technetium, Ruthenium, Rhodium, Palladium, Silver, Cadmium, Indium, Tin, Antimony, Tellurium, Iodine, Xenon, Caesium, Barium, Lanthanum, Cerium, Praseodymium, Neodymium, Promethium, Samarium, Europium, Gadolinium, Terbium, Dysprosium, Holmium, Erbium, Thulium, Ytterbium, Lutetium, Hafnium, Tantalum, Tungsten, Rhenium, Osmium, Iridium, Platinum, Gold, Mercury, Thallium, Lead, Bismuth, Polonium, Astatine, Radon, Francium, Radium, Actinium, Thorium, Protactinium and/or Uranium.

In an embodiment of the method for identifying the elemental composition of and/or quantifying the presence of mono-isotopic elements in a molecule in a sample, said molecule comprises at least one mono-isotopic constituent atom in its chemical formula, and the method further comprises a combination of the steps of:

obtaining from said isotopic distribution a measured mass within a precision of ±0.9 Da, ±0.8 Da, ±075 Da, ±0.6 Da, ±0.5 Da, ±0.4 Da, ±0.3 Da, ±025 Da, ±0.1 Da at which an isotope peak appears;

computing an expected mass at which said isotope peak appears for a second molecule with a second chemical formula which is said chemical formula from which the mono-isotopic constituent atom is removed;

comparing said measured mass with said expected mass to deduce the presence of said molecule comprising at least one mono-isotopic constituent atom in said sample.

It is one of the advantages of the present method for identifying the elemental composition of and/or quantifying the presence of mono-isotopic elements in a molecule in a sample, that it is able to derive the values of $n_\alpha$ for at least one and possibly each value of $\alpha$ in the chemical formula of a molecule, on this only from the relative peak size of at least part of an aggregated isotopic distribution. One does not require the exact and/or center masses at which these peaks are observed. However, this method can only identify values of $n_\alpha$ for atomic species with at least two stable isotopes. When a molecule comprises at least one mono-isotopic atomic species, this species does not alter the isotopic distribution or the aggregated isotopic distribution with respect to the peak heights. It will only result in a change of the masses at which the peaks are observed. Therefore, when employing the method described here above, one can compute how much of the mass of a molecule of which an isotopic distribution is measured or observed arises from mono-isotopic atomic species constituting the molecule. For this, one needs to compare at least one mass at which an aggregated isotopic variant is observed with the mass of this aggregated isotopic variant as computed from the chemical formula of the molecule as derived using a method for identifying the elemental composition of and/or quantifying the presence of mono-isotopic elements in a molecule in a sample as described in this text. Hereby, the difference in mass can be attributed to non-mono-isotopic atomic species comprised in the molecule present in the sample. The thus obtained mass difference can be compared with the masses of mono-isotopic atomic species. In a preferred embodiment of the method for identifying the elemental composition of and/or quantifying the presence of mono-isotopic elements in a molecule in a sample, said at least one mono-isotopic constituent atom is phosphorus-31. In another preferred embodiment, said mass difference is attributed to a combination of the following mono-isotopic elements present in the molecule: Beryllium-9, Fluorine-19, Sodium-23, Aluminium-27, Phosphorus-31, Scandium-45, Vanadium-51, Manganese-55, Cobalt-59, Arsenic-75, Rubidium-85, Yttrium-89, Niobium-93, Rhodium-103, Indium-113, Iodine-127, Caesium-133, Lanthanum-139, Praseodymium-141, Europium-153, Terbium-159, Holmium-165, Thulium-169, Lutetium-175, Rhenium-185, Gold-197.

In a further aspect, the present invention provides a device capable of identifying the presence, elemental composition and/or quantity of a molecule in a sample using the method as described above. Preferably, this device comprises a mass-spectrometric set-up or is a mass spectrometer with corresponding analyzing apparatus. The device may also comprise a computer implemented with the above described method.

In still another aspect, the present invention provides a computer-mountable device comprising an implementation of the method for identifying the elemental composition of and/or quantifying the presence of mono-isotopic elements in a molecule in a sample as described in this document. Such a computer-mountable device can be a hard disk, a floppy disk, a USB stick or other kind of flash-memory, an internet connection to a database or website where an implementation of such a method is available.

In yet another aspect, the present invention provides a use of a method for identifying the elemental composition of and/or quantifying the presence of mono-isotopic elements in a molecule in a sample as described in this document, preferably on a computer and/or a mass spectrometer and/or a peripheral instrument of a mass spectrometer and/or any other apparatus.

The invention is further described by the following non-limiting examples which further illustrate the invention, and are not intended to, nor should they be interpreted to, limit the scope of the invention.

It is supposed that the present invention is not restricted to any form of realization described previously and that some modifications can be added to the presented methodology and/or devices without reappraisal of the appended claims. For example, the present invention has been described in this document mostly referring to polypeptide molecules, but it is clear that the invention can be applied to all molecule.

EXAMPLES

Example 1

For carbon monoxide, CO, one may choose $A_0=28$, i.e. the lightest mono-isotopic variant. One then easily computes $q_0=P(_6^{12}C)P(_8^{16}O)=0.986896001$. To compute the probability $q_1$ with which the aggregated isotopic variant of CO with mass number $A_1=29$ occurs, one can use $q_1=\Sum_{j=0}^{0} C_{1,0} q_0$ with $$C_{1,0} = -\frac{\rho-1}{1} \text{ and}$$

$$\rho_{-1} = r_C^{-1} + r_O^{-1} + \bar{r}_O^{-1}, \text{ whereby}$$

$$r_C = -\frac{P(_6^{12}C)}{P(_6^{13}C)},$$

$$r_O = \frac{-P(_8^{17}O) + \sqrt{P(_8^{17}O)^2 - 4P(_8^{16}O)P(_8^{18}O)}}{2P(_8^{18}O)} \text{ and}$$

$$\bar{r}_O = \frac{-P(_8^{17}O) - \sqrt{P(_8^{17}O)^2 - 4P(_8^{16}O)P(_8^{18}O)}}{2P(_8^{18}O)}$$

are the roots of the equations $P(_6^{12}C)+P(_6^{13}C)I=0$ and $P(_8^{16}O)+P(_8^{17}O)I+P(_8^{18}O)I^2=0$. This leads to $\rho_{-1}=-0.011196653942$ and $q_1=0.011049933$. In the following steps, one obtains $\rho_{-2}=r_C^{-2}+r_O^{-2}+\bar{r}_O^{-2}=-0.003992862186$ and $q_2=0.002032131$, and $\rho_{-3}=r_C^{-3}+r_O^{-3}+\bar{r}_O^{-3}=0.000001083120$ and $q_3=0.000021935$. These numbers are summarized in the table below:

| i | $A_i$ | $\rho_{-i} = r_C^{-i} + r_O^{-i} + \bar{r}_O^{-i}$ | $q_i$ |
|---|---|---|---|
| 0 | 28 | — | 0.986896001 |
| 1 | 29 | −0.011196653942 | 0.011049933 |
| 2 | 30 | −0.003992862186 | 0.002032131 |
| 3 | 31 | 0.000001083120 | 0.000021935 |

For $C_3H_8$, a similar table may be constructed:

| i | $A_i$ | $\rho_{-i} = r_C^{-i} + r_O^{-i} + \bar{r}_O^{-i}$ | $q_i$ |
|---|---|---|---|
| 0 | 44 | — | 0.967351820549 |
| 1 | 45 | −0.033367290690 | 0.032277909396 |
| 2 | 46 | 0.000351045760 | 0.000368720815 |
| 3 | 47 | −0.000003795683 | 0.000001547984 |
| 4 | 48 | 0.000000041053 | 0.000000001255 |
| 5 | 49 | −0.000000000444 | 0.000000000000 |
| 6 | 50 | 0.000000000005 | 0.000000000000 |
| ... | | | |

It is seen from this table that only the first few peaks can be observed in a MS measurement.

Example 2

Example on the Computation of the Center Masses of the Aggregated Isotopic Variants of CO An isotopic distribution of a sample is provided, and one wants to analyze the sample for CO. Hereby, one wants to compare part of the measured isotopic distribution with the aggregated isotopic distribution, also with respect to the center masses. Hereby, one needs to obtain this aggregated isotopic distribution and the center masses. Afterwards, one can make the comparison between the aggregated isotopic distribution and the center masses as obtained, and the aggregated isotopic distribution as derived from the measured isotopic distribution.

Previously, we have already explained the isotopic distribution of the molecule CO.

For the lightest variant, which we can take as the starting or zeroth variant, one has:

$$A_0 = A(_6^{12}C) + A(_8^{16}O) = 28,$$

$$M_0 = M(_6^{12}C) + M(_8^{16}O) = 27.995\ Da,$$

$$q_0 = P(_6^{12}C)P(_8^{16}O) = 0.986896001.$$

Note that, since it is a mono-isotopic variant, the center mass is also the isotopic mass.

Obviously, the center mass of a mono-isotopic variant is easily computed by summing the masses of the constituting isotopes, i.e. $M_0 = M(_6^{12}C) + M(_8^{16}O) = 27.995$ Da. However, we will illustrate in the following that the method as described in this text can also be applied to mono-isotopic variants.

The isotope $_6^{12}C$ occurs in the zeroth (aggregated) isotopic variant of CO with probability=1. Therefore, weighted average mass of the Carbon atomic species in the lightest isotopic variant of CO is given by $$p_0^c = P(_6^{12}C)P(_8^{16}O)M(_6^{12}C) = 11.842752012\ Da,$$

since this weighted average mass should be normalized to the probability $q_0 = P(_6^{12}C)P(_8^{16}O)$, i.e. if the masses of all atomic isotopes were 1, the weighted average mass $p_0^c$ would equal the probability $q_0$.

A similar computation for O leads to $$p_0^O = P(_6^{12}C)P(_8^{16}O)M(_8^{16}O) = 15.785317274\ Da.$$

The center mass for the lightest aggregated isotopic variant is then easily computed as $$M_0 = \frac{p_0^C + p_0^O}{q_0}$$

$$= \frac{(_6^{12}C)P(_8^{16}O)M(_6^{12}C) + P(_6^{12}C)P(_8^{16}O)M(_8^{16}O)}{P(_6^{12}C)P(_8^{16}O)}$$

$$= M(_6^{12}C) + M(_8^{16}O)$$

$$= 27.995 Da.$$

The computation of the center mass of the aggregated isotopic variant with molecular mass number 29 is slightly more complicated. One has two contributing isotopic variants. $^{13}C^{16}O$ with $$\text{abundance}\ p_{1,0} = P(_6^{13}C)P(_8^{16}O) = 0.010673999$$

$$\text{mass}\ m_{1,0} = M(_6^{13}C) + M(_8^{16}O) = 28.9982695\ Da$$

and $^{12}C^{17}O$ with $$\text{abundance}\ p_{1,1} = P(_6^{12}C)P(_8^{17}O) = 0.000375934$$

$$\text{mass}\ m_{1,1} = M(_6^{12}C) + M(_8^{17}O) = 28.9991317 Da$$

and total abundance $$q_1 = p_{1,0} + p_{1,1} = 0.011049933.$$

The isotope $_6^{12}C$ occurs in the first aggregated isotopic variant of CO with a probability directly proportional to the relative abundance $p_{1,1}$ with which isotopic variant $^{12}C^{17}O$ contributes to the first aggregated isotopic variant. The isotope $_6^{13}C$ occurs in the first aggregated isotopic variant of CO with a probability directly proportional to the relative abundance $p_{1,0}$ with which isotopic variant $^{13}C^{16}O$ contributes to the first aggregated isotopic variant. Therefore, the weighted average mass of the Carbon atomic species in the first aggregated isotopic variant of CO is given by $$p_1^c = p_{1,0}M(_6^{13}C) + p_{1,1}M(_6^{12}C) = P(_6^{13}C)P(_8^{16}O)$$
$$M(_6^{13}C) + P(_6^{12}C)P(_8^{17}O)M(_6^{12}C) = 0.14331\ Da$$

A similar computation for O leads to $$p_1^O = p_{1,0}M(_8^{16}O) + p_{1,1}M(_6^{17}O) = P(_6^{13}C)P(_8^{16}O)$$
$$M(_8^{16}O) + P(_6^{12}C)P(_8^{17}O)M(_8^{17}O) = 0.17712\ Da$$

Note again, that if one puts all masses of all isotopes equal to one, the weighted average masses of both Carbon as Oxygen species would equal $q_1$, i.e. the weighted average masses are normalized to $q_1$.

The center mass for the first aggregated isotopic variant is then computed as $$M_1 = \frac{p_1^C + p_1^O}{q_1}$$

$$= \frac{P(_6^{13}C)P(_8^{16}O)[M(_6^{13}C) + M(_8^{16}O)] + P(_6^{12}C)P(_8^{17}O)[M(_6^{12}C) + M(_6^{17}O)]}{P(_6^{13}C)P(_8^{16}O) + P(_6^{12}C)P(_8^{17}O)}$$

$$= \frac{p_{1,0}m_{1,0} + p_{1,1}m_{1,1}}{q_1}$$

$$= 28.99838888 Da,$$

which clearly is a value between the masses of the two isotopic variants, closer to the mass of the more prominent variant $^{13}C^{16}O$.

For the second aggregated isotopic variant, one obtains for the weighted average masses, e.g. by taking a linear combination of the already computed weighted average masses $p_2^{c,o} = \sum_{j=0}^{1} D_{2,j}^{c,o} p_j^{c,o}$, whereby the coefficients aree computed as follows:

$$D_{2,0}^C = -\frac{1}{2}[(r_C^{-2} + r_O^{-2} + \bar{r}_O^{-2}) - r_C^{-2} + s_C^{-2}]$$

$$D_{2,1}^C = -\frac{1}{2}[(r_C^{-1} + r_O^{-1} + \bar{r}_O^{-1}) - r_C^{-1} + s_C^{-1}]$$

$$D_{2,0}^O = -\frac{1}{2}[(r_C^{-2} + r_O^{-2} + \bar{r}_O^{-2}) - r_O^{-2} + s_O^{-2}]$$

$$D_{2,1}^O = -\frac{1}{2}[(r_C^{-1} + r_O^{-1} + \bar{r}_O^{-1}) - r_O^{-1} + s_O^{-1}]$$

Using eqs. (EL.10) and (EL.11) for the roots $r_{c,o}$, and similar expressions (changing the atomic isotopic abundancies in (EL.10) and (EL.11) by the product of the atomic isotopic abundancies and the atomic isotopic masses) for the roots $s_{c,o}$, one obtains $$p_2^C = D_{2,0}^C p_0^C + D_{2,1}^C p_1^C = P(_6^{13}C)P(_8^{17}O)M(_6^{13}C) + P(_6^{12}C)P(_8^{18}O)M(_6^{12}C) = 0.024389652 \text{ Da},$$

$$p_2^O = D_{2,0}^O p_0^O + D_{2,1}^O p_1^O = P(_6^{13}C)P(_8^{17}O)M(_8^{17}C) + P(_6^{12}C)P(_8^{18}O)M(_6^{18}C) = 0.036572587 \text{ Da},$$

with probability $$q_2 = P(_6^{13}C)P(_8^{17}O) + P(_6^{12}C)P(_8^{18}O) = 0.002032131.$$

This gives for the center mass $$M_2 = \frac{p_2^C + p_2^O}{q_2} = 29.9991678 Da.$$

For the third aggregated isotopic variant, which is the heaviest and thus a mono-isotopic variant, one can still use the same procedure as above, leading to $p_3^{C,O} = \sum_{j=0}^{2} D_{3,j}^{C,O} p_j^{C,O}$ with $$D_{3,0}^C = -\frac{1}{3}[(r_C^{-3} + r_O^{-3} + \bar{r}_O^{-3}) - r_C^{-3} + s_C^{-3}]$$

$$D_{3,1}^C = -\frac{1}{3}[(r_C^{-2} + r_O^{-2} + \bar{r}_O^{-2}) - r_C^{-2} + s_C^{-2}]$$

$$D_{3,2}^C = -\frac{1}{3}[(r_C^{-1} + r_O^{-1} + \bar{r}_O^{-1}) - r_C^{-1} + s_C^{-1}]$$

$$D_{3,0}^O = -\frac{1}{3}[(r_C^{-3} + r_O^{-3} + \bar{r}_O^{-3}) - r_O^{-3} + s_O^{-3}]$$

$$D_{3,1}^O = -\frac{1}{3}[(r_C^{-2} + r_O^{-2} + \bar{r}_O^{-2}) - r_O^{-2} + s_O^{-2}]$$

$$D_{3,2}^O = -\frac{1}{3}[(r_C^{-1} + r_O^{-1} + \bar{r}_O^{-1}) - r_O^{-1} + s_O^{-1}]$$

This leads to $$p_3^C = D_{3,0}^C p_0^C + D_{3,1}^C p_1^C = P(_6^{13}C)P(_8^{18}O)M(_6^{13}C) = 0.0002852286 \text{ Da},$$

$$p_3^O = D_{3,0}^O p_0^O + D_{3,1}^O p_1^O = P(_6^{13}C)P(_8^{18}O)M(_6^{18}C) = 0.0003948116 \text{ Da},$$

with probability $$q_3 = P(_6^{13}C)P(_8^{18}O) = 0.000021935.$$

This gives for the center mass $$M_3 = \frac{p_3^C + p_3^O}{q_3} = 31.00252 Da,$$

which can be observed to equal the mass of the heaviest isotope variant $^{13}C^{18}O$: $M(_6^{13}C) + M(_8^{18}O)$.

Example 3

Example on the Computation of the Chemical Formula when an Isotopic Distribution is Provided FIG. 1 presents the aggregated isotopic distribution of a molecule in a sample as observed by mass spectrometry, whereby the peaks of the aggregated isotopic variants are indicated with dots (1), and whereby the distribution at lower m/z values (2) can be attributed to the unphosphorylated molecules, while the distribution observed at higher m/z values (3) can be attributed to the phosphorylated molecules.

The molecule under scrutiny in FIG. 1 is Beta-caseine with a mono-isotopic mass of 23568.3197 Da for the unphosphorylated molecules. The molecule has a charge of z equal to 8. Therefore, the observed mono-isotopic mass in term of m/z equals (23568.3197+8)/8. The reversed calculation can be applied to calculate the mono-isotopic mass based on the observed m/z and z. For example, the observed mono-isotopic peak is observed at 2947.04779227045 m/z. The charge of the molecules is 8, hence 2947.04779227045×8−8=23568.3823381636 Da is the mass of the lightest mono-isotopic variant. The distribution around m/z=2949 (2) is caused by the unphosphorylated variant of Beta-casein while the distribution around m/z=2959 (3) is caused by the phosphorylated variant. A single phosphorylation causes a mass shift of 80 dalton due to the addition of $HPO_3$. From the observed distribution (2) the peak heights and their ranks in the aggregated distribution are extracted by using a peak extraction algorithm according to the present invention. The detected peaks are indicated by dots (1) and the result is listed below:

$$t_1 = 100000$$

$$t_2 = 1303159.40498057$$

$$t_3 = 8575419.36617413$$

...

$$t_{50} = 2.39573123747609.$$

These peak heights can be transformed to ratio-like numbers using Eqs. (9a) and (9b) as follows:

$$\hat{t}_1 = -1/t_1 \times t_2 = -13.0315940498057$$

$$\hat{t}_2 = -1/t_1 \times (2 \times t_3 + \hat{t}_1 \times t_2) = -1.6859438445517$$

$$\hat{t}_3 = -1/t_1 \times (3 \times t_4 + \hat{t}_2 \times t_2 + \hat{t}_1 \times t_3) = 0.00585728955879807$$

...

$$\hat{t}_{49} = -1/t_1 \times (49 \times t_{50} + \hat{t}_{48} \times t_2 + \hat{t}_{47} \times t_3 + \ldots + \hat{t}_1 \times t_{49}) =$$
$$1.3669076173386e-008.$$

Meanwhile, based on the rank information and the roots of the five putative elements (C,H,N,O,S) a 49×5 matrix A is constructed. Example 1 explains how the roots can be calculated. The five columns of matrix A contain a power sum of the roots of C, H, N, O and S, respectively. The power of the power sum is determined by the row index. For example, Matrix A=

Row 1: $[r_C^{-1}, r_H^{-1}, r_N^{-1}, r_O^{-1} + \bar{r}_O^{-1}, r_{1,S}^{-1} + \bar{r}_{1,S}^{-1} + r_{2,S}^{-1} + \bar{r}_{2,S}^{-1}]$ Row 2: $[r_C^{-2}, r_H^{-2}, r_N^{-2}, r_O^{-2} + \bar{r}_O^{-2}, r_{1,S}^{-2} + \bar{r}_{1,S}^{-2} + r_{2,S}^{-2} + \bar{r}_{2,S}^{-2}]$ Row 3: $[r_C^{-3}, r_H^{-3}, r_N^{-3}, r_O^{-3} + \bar{r}_O^{-3}, r_{1,S}^{-3} + \bar{r}_{1,S}^{-3} + r_{2,S}^{-3} + \bar{r}_{2,S}^{-3}]$

...

Row 49: $[r_C^{-49}, r_H^{-49}, r_N^{-49}, r_O^{-49} + \bar{r}_O^{-49}, r_{1,S}^{-49} + \bar{r}_{1,S}^{-49} + r_{2,S}^{-49} + \bar{r}_{2,S}^{-49}]$.

The solution of the system of equations, $\hat{t}=A.M$, whereby M is a column matrix of the values $n_\alpha$ for atomic species $\alpha$=C,H,N,O,S, gives an estimate of the elemental composition of the sample assayed by mass spectrometry. In this case we solve the system of equation with a least-square method and consecutive rounding. This results in following estimates:

$n_C$=1080

$n_H$=1699

$n_N$=268

$n_O$=310

$n_S$=6.

It should be noted that if a different peak height or linear combination of peak heights was used as reference, i.e. when $t_1$ was replaced by another number, the same solution for the values of $n_\alpha$ would have been obtained trivially by using a rescaled matrix A.

Based on previous results the mono-isotopic mass is calculated as explained in Example 2. This leads to 23575.3745131315 Da. Since the molecule has a charge of eight, we need to subtract this number of hydrogen atoms. This gives 23567.3745131315 Da. It should be noted that due to the simplistic optimization, signal variation and nearest rounding a small misestimate of one hydrogen atom has occurred.

Example 4

Example on the Observation of the Presence of a Phosphorus Atom in a Molecule of which the Isotopic Distribution is Provided The procedure explained in Example 3 is repeated for the heavier distribution (3). This results in estimates:

$n_C$=1080

$n_H$=1699

$n_N$=268

$n_O$=310

$n_S$=6.

The mono-isotopic mass is calculated by using previous results as 23623.3592569315 Da. After subtraction of the eight hydrogen atoms, we obtain: 23615.3592569315 Da. The mono-isotopic mass of the heavier distribution (3) is observed at 2957.04358337446 m/z or equivalently at a mass of 2957.04358337446×8-8=23648.3486669957 Da. The difference between the observed mass and the estimated mass based on the observed distribution is 23648.3486669957-23615.3592569315=32.9894100641977. Again a small error occurred when estimating the number of hydrogen atoms. In this case, two hydrogen atoms where missed. However, the discrepancy between observed and estimated mass is too large to be explained by rounding errors. Therefore, we conclude that the mass difference is due to the presence of a mono-isotopic element. The element closest to 32.9894100641977 Da is phosphorus with a mass of 30.97376 Da.

What is claimed is:

1. Method for identifying the elemental composition of a molecule and/or quantifying the presence of mono-isotopic elements in a molecule in a sample, whereby said molecule has a chemical formula $\Pi_\alpha(Z_\alpha)_{n_\alpha}$ with
    $\alpha$ an index running over a number of expected constituent atomic species of said molecule;
    $Z_\alpha$ the $\alpha$'th expected atomic species of the molecule; and
    $n_\alpha$ the number of atoms of species $Z_\alpha$ in the molecule,
    comprising the steps of:
    obtaining at least a part of an isotopic distribution from said sample by ionizing the molecules to generate charged molecules or molecule fragments and measuring a mass-to-charge ratio of the charged molecules or molecule fragments;
    obtaining a set of $N_p$ peak heights $t_j$ with j=1 ... $N_p$, of at least part of an aggregated isotopic distribution from said isotopic distribution;
    computing from said set of peak heights a set of $N_p$-1 ratios of peak heights $\hat{t}_i$ with i=1 ... $N_p$-1;
    obtaining a value of $n_\alpha$ for at least one atomic species $Z_\alpha$ from said set of ratios of peak heights,
    wherein said value of $n_\alpha$ is obtained by computing a solution of a system of linear equations $\Sigma_\alpha E_{i\alpha} n_\alpha = F_i$, whereby the set of numbers $F_i$ comprises said set of ratios of peak heights and the coefficients $E_{i\alpha}$ of said linear system comprise powers and/or power sums of roots $r_{\alpha,i_\alpha}$, with $i_\alpha$=1 ... $N_\alpha$, of an $N_\alpha$'th-order elemental polynomial equation whose coefficient of the $m_\alpha$'th order term is given by an elemental abundance $$P\binom{A_\alpha + m_\alpha}{Z_\alpha} Z_\alpha$$

of the isotope of the atom species $Z_\alpha$ with $m_\alpha$ neutrons more than the lightest stable isotope of said atom species which has atomic mass number $A_\alpha$, whereby the masses at which the peak heights $t_j$ are observed are essentially 1 Da apart, whereby said set of $N_p$-1 ratios of peak heights $\hat{t}_i$ with i=1 ... $N_p$-1 is computed recursively from said set of $N_p$ peak heights $t_j$ with j=1 ... $N_p$, using the steps of:

computing $\hat{t}_1 = -\dfrac{t_2}{t_1}$;

computing $\hat{t}_{i+1} = -\dfrac{1}{t_1}\left[(i+1)t_{i+2} + \sum_{j=1}^{i} \hat{t}_{i-j+1} t_{j+1}\right]$ for $i = 2 \ldots N_p - 1$.

2. Method for identifying the elemental composition of a molecule and/or quantifying the presence of mono-isotopic elements in a molecule in a sample according to claim 1, whereby said set of peak heights $t_j$ is ordered according to the mass at which a peak height is observed, whereby no peak is observed in said isotopic distribution or said aggregated isotopic distribution around a mass which is essentially 1 Da smaller than the mass at which the first of said set of peak heights $t_j$ i.e. $t_1$, is observed, whereby said coefficients of said linear system are given by the sum of the $(-i)$'th power of the $N_\alpha$ roots of the $N_\alpha$'th-order elemental polynomial equation whose coefficient of the $m_\alpha$'th-order term is given by the elemental abundance $P(_{Z_\alpha}^{A_\alpha+m_\alpha}Z_\alpha)$ of the isotope of atomic species $Z_\alpha$ with $m_\alpha$ neutrons more than the lightest stable isotope of said atomic species which has atomic mass number $A_\alpha$, i.e. $E_{i\alpha}=\Sigma_{i_\alpha=1}^{N_\alpha} r_{\alpha,i_\alpha}^{-i}$, and whereby said set of numbers $F_i$ is given by said set of ratios of peak heights $\hat{t}_i$, i.e. $F_i=\hat{t}_i$, and whereby said number $N_p-1$ of ratios of peaks heights is at least said number of expected constituent atomic species of said molecule with two or more stable isotopes.

3. Method for identifying the elemental composition of a molecule and/or quantifying the presence of mono-isotopic elements in a molecule in a sample according to claim 1, whereby said expected atomic species comprise carbon, hydrogen, nitrogen, oxygen and/or sulfur.

4. Method for identifying the elemental composition of a molecule and/or quantifying the presence of mono-isotopic elements in a molecule in a sample according to claim 1, whereby said molecule comprises at least one mono-isotopic constituent atom in its chemical formula, further comprising the steps of:
  obtaining from said isotopic distribution a measured mass within a precision of ±0.5 Da at which an isotope peak appears;
  computing an expected mass at which said isotope peak appears for a second molecule with a second chemical formula which is said chemical formula from which the mono-isotopic constituent atom is removed;
  comparing said measured mass with said expected mass to deduce the presence of said molecule comprising at least one mono-isotopic constituent atom in said sample,
whereby said at least one mono-isotopic constituent atom is phosphorus.

5. Device capable of identifying the elemental composition of a molecule and/or quantifying the presence of mono-isotopic elements in a molecule in a sample, wherein the device comprises a mass spectrometric setup comprising an ion source, a mass analyzer and a detector such that the mass spectrometric setup is configured to ionize the molecules to generate charged molecules or molecule fragments and measure a mass-to-charge ratio of the charged molecules or molecule fragments, and a computing unit functionally connected to the mass spectrometric setup, the computing unit arranged to identify the elemental composition of a molecule and/or quantifying the presence of mono-isotopic elements in a molecule in a sample whereby said molecule has a chemical formula $\Pi_\alpha(Z_\alpha)\, n_\alpha$ with
  $\alpha$ an index running over a number of expected constituent atomic species of said molecule;
  $Z_\alpha$ the $\alpha$'th expected atomic species of the molecule; and
  $n_\alpha$ the number of atoms of species $Z_\alpha$ in the molecule,
wherein the method comprises the steps of:
  obtaining at least a part of an isotopic distribution from said sample;
  obtaining a set of $N_p$ peak heights $t_j$ with $j=1 \ldots N_p$, of at least part of an aggregated isotopic distribution from said isotopic distribution;
  computing from said set of peak heights a set of $N_p-1$ ratios of peak heights $\hat{t}_i$ with $i=1 \ldots N_p-1$;
  obtaining a value of $n_\alpha$ for at least one atomic species $Z_\alpha$ from said set of ratios of peak heights,
wherein said value of $n_\alpha$ is obtained by computing a solution of a system of linear equations $\Sigma_\alpha E_{i\alpha} n_\alpha = F_i$, whereby the set of numbers F comprises said set of ratios of peak heights and the coefficients $E_{i\alpha}$ of said linear system comprise powers and/or power sums of roots $r_{\alpha,i_\alpha}$, with $i_\alpha=1 \ldots N_\alpha$, of an $N_\alpha$'th-order elemental polynomial equation whose coefficient of the $m_\alpha$'th order term is given by an elemental abundance $P(_{Z_\alpha}^{A_\alpha+m_\alpha}Z_\alpha)$ of the isotope of the atom species $Z_\alpha$ with $m_\alpha$ neutrons more than the lightest stable isotope of said atom species which has atomic mass number $A_\alpha$, whereby the masses at which the peak heights $t_j$ are observed are essentially 1 Da apart, whereby said set of $N_p-1$ ratios of peak heights $\hat{t}_i$ with $i=1 \ldots N_p-1$ is computed recursively from said set of $N_p$ peak heights $t_j$ with $j=1 \ldots N_p$, using the steps of:

computing $\hat{t}_1 = -\dfrac{t_2}{t_1}$;

computing $\hat{t}_{i+1} = -\dfrac{1}{t_1}\left[(i+1)t_{i+2} + \sum_{j=1}^{i} \hat{t}_{i-j+1} t_{j+1}\right]$ for $i = 2 \ldots N_p - 1$.

* * * * *